(12) United States Patent
Choi et al.

(10) Patent No.: US 11,718,687 B2
(45) Date of Patent: Aug. 8, 2023

(54) BIOMOLETRON FOR REGULATION STEM CELL DIFFERENTIATION

(71) Applicant: SOGANG UNIVERSITY RESEARCH FOUNDATION, Seoul (KR)

(72) Inventors: Jeong Woo Choi, Seoul (KR); Sang Uk Kim, Seoul (KR); Jin Ho Yoon, Seoul (KR); Mohsen Mohammadniaei, Seoul (KR)

(73) Assignee: SOGANGN UNIVERSITY RESEARCH FOUNDATION, Seoul (KR)

( * ) Notice: Subject to any disclaimer, the term of this patent is extended or adjusted under 35 U.S.C. 154(b) by 810 days.

(21) Appl. No.: 16/075,790

(22) PCT Filed: Mar. 29, 2016

(86) PCT No.: PCT/KR2016/003208
§ 371 (c)(1),
(2) Date: Aug. 6, 2018

(87) PCT Pub. No.: WO2017/159911
PCT Pub. Date: Sep. 21, 2017

(65) Prior Publication Data
US 2019/0202939 A1  Jul. 4, 2019

(30) Foreign Application Priority Data

Mar. 17, 2016  (KR) ........................ 10-2016-0032252

(51) Int. Cl.
C12M 1/42  (2006.01)
C07K 17/14  (2006.01)
C07K 19/00  (2006.01)
C12N 5/00  (2006.01)

(52) U.S. Cl.
CPC .............. *C07K 19/00* (2013.01); *C07K 17/14* (2013.01); *C12M 35/02* (2013.01); *C12N 5/00* (2013.01)

(58) Field of Classification Search
None
See application file for complete search history.

(56) References Cited

U.S. PATENT DOCUMENTS

2009/0123467 A1  5/2009  Bedi et al.

FOREIGN PATENT DOCUMENTS

| KR | 1020090034239 A | 4/2009 |
| KR | 1020130068936 A | 6/2013 |
| KR | 1020150003617 A | 1/2015 |

OTHER PUBLICATIONS

Mallapragada, S.K, et al. 2015 Nanomedicine: Nanotechnology, Biology, and Medicine 11: 715-729. (Year: 2015).*
Solanki, A., et al. 2013 Scientific Reports 3, 1553: 1-7. (Year: 2013).*
Jiang, Y., et al. 2016 Expert Opinion on Drug Delivery 13(4): 547-559, published online Jan. 18, 2016. (Year: 2016).*
Kim, S-U., et al. 2010 J Nanosci Nanotechnol 10(5): 3241-3245. (Year: 2010).*
Min, J., et al. 2008 J Nanosci Nanotechnol 8(10): 4982-4987. (Year: 2008).*
Kim, S-U., et al. 2008 Korean J Chem Eng 25(5): 1115-1119. (Year: 2008).*
K. -A. Chang, et al., "Biphasic Electrical Currents Stimulation Promotes both Proliferation and Differentiation of Fetal Neural Stem Cells", PLoS ONE, 6, e18738 (2011), 11 pgs.
Y. -J. Huang, et al., "Carbon Nanotube Rope with Electrical Stimulation Promotes the Differentiation and Maturity of Neural Stem Cells", Small, 8, 2869 (2012), 9 pgs.
J. T. Robinson, et al., "Vertical nanowire electrode arrays as a scalable platform for intracellular interfacing to neuronal circuits", Nature Nanotechnology, 7, 180 (2012), 5 pgs.
C. Liu, et al., "A Fully Integrated Nanosystem of Semiconductor Nanowires for Direct Solar Water Splitting", Nano Letters, 13, 2989 (2013), 4 pgs.
O. Yanes, et al., "Metabolic oxidation regulates embryonic stem cell differentiation", Nature chemical biology, 6, 411 (2010), 5 pgs.
K. Wang, et al., "Redox homeostasis: the linchpin in stem cell self-renewal and differentiation", Cell death and disease, 4, e537 (2013), 10 pgs.
Y. Yan, et al., "The antioxidant enzyme Prdx1 controls neuronal differentiation by thiol-redox dependent activation of GDE2", Cell, 138, 1209 (2009), 22 pgs.
M. K. Hossain, et al., "In situmonitoringofdoxorubicinreleasefrom biohybridnanoparticles modified withantibodyandcell-penetratingpeptidesinbreastcancer cells usingsurface-enhancedRamanspectroscopy", Biosensors and Bioelectronics, 71, 300 (2015), 6 pgs.
Feng Tian et al., "Peptide Separation through a CB[8]-Mediated Supramolecular Trap-and-Release Process†", Langmuir, 27, 4, (2011), 4 pgs.
Yagati, Ajay Kumar et al.. "STM and Cyclic Voltammetric Investigation of Recombinantazurin-gold Nanoparticle Hybrids", Bioelectrochemistry, [E-pub.] Jul. 27, 2011, vol. 83, pp. 8-14, 7 pgs.
International Search Report and Written Opinion dated Dec. 16, 2016 of corresponding application No. PCT/KR2016/003208; 7 pgs.

* cited by examiner

*Primary Examiner* — Marsha Tsay
(74) *Attorney, Agent, or Firm* — Harness, Dickey & Pierce, P.L.C.

(57) ABSTRACT

A bioelectronic device for regulating stem cell differentiation, a method for differentiating stem cells using the same, and a method for manufacturing the bioelectronic device. According to the present invention, it is possible to effectively control the differentiation of stem cells at a single-cell level, and to simultaneously perform a free radical inhibition function.

11 Claims, 18 Drawing Sheets

Specification includes a Sequence Listing.

Redox protein modification

Redox protein

Azurin
-electron control
-free radical control

→

Recombinant redox protein

RGD

Modification points

Multi Site-Directed Mutagenesis (MSDM)
- Three cysteine group
- N-teminal: DNA binding site
- C-terminal: RGD sequence PAGE Lanes:
(1) Protein Marker
(2) pET21-sukim-3D-Azurin-Cys-Ct-RGD 75 type
(3) pET21-sukim-3D-Azurin-Cys-Ct-RGD 69 type
(4) pET21-sukim-3D-Azurin-Cys-Ct-RGD 41 type
(5) pET21-sukim-3D-Azurin-Cys-Ct-RGD 35 type

SEQUENCE LISTING

```
<160> NUMBER OF SEQ ID NOS: 68

<210> SEQ ID NO 1
<211> LENGTH: 456
<212> TYPE: DNA
<213> ORGANISM: Artificial Sequence
<220> FEATURE:
<223> OTHER INFORMATION: recombinant azurin

<400> SEQUENCE: 1
atgctacgta aactcgctgc cgtatccctg ctgtccctgc tcagtgcgcc gctgctggct      60
gccgagtgct cggtggacat ccagggtaac gaccagtgcc agttcaacac caatgccatc     120
accgtcgaca gagctgcaa gcagttcacc gtcaacctgt cccaccccgg caactgcccg      180
aagaacgtca tgggccacaa ctgggtactg agcaccgccg ccgacatgca gggcgtggtc     240
accgacggca tggcttccgg cctggacaag gattacctga agcccgacga cagccgcgtc     300
atcgcccaca ccaagctgat cggctcgggc gagtgcgact cggtgacctt cgacgtctcc     360
aagctgaagg aaggcgagca gtacatgttc ttctgcacct cccgggcca ctccgcgctg      420 atgaagggca ccctgaccct gaagcgcggg gattga                              456

<210> SEQ ID NO 2
<211> LENGTH: 150
<212> TYPE: PRT
<213> ORGANISM: Artificial Sequence
<220> FEATURE:
<223> OTHER INFORMATION: recombinant azurin

<400> SEQUENCE: 2

Met Leu Arg Lys Leu Ala Ala Val Ser Leu Leu Ser Leu Leu Ser Ala
1               5                   10                  15

Pro Leu Leu Ala Ala Glu Cys Ser Val Asp Ile Gln Gly Asn Asp Gln
                20                  25                  30

Cys Gln Phe Asn Thr Asn Ala Ile Thr Val Asp Lys Ser Cys Lys Gln
            35                  40                  45

Phe Thr Val Asn Leu Ser His Pro Gly Asn Cys Pro Asn Val Met Gly
        50                  55                  60

His Asn Trp Val Leu Ser Thr Ala Ala Asp Met Gln Gly Val Val Thr
    65                  70                  75                  80

Asp Gly Met Ala Ser Gly Leu Asp Lys Asp Tyr Leu Lys Pro Asp Asp
                85                  90                  95

Ser Arg Val Ile Ala His Thr Lys Leu Ile Gly Ser Gly Glu Cys Asp
                100                 105                 110

Ser Val Thr Phe Asp Val Ser Lys Leu Lys Glu Gly Glu Gln Tyr Met
            115                 120                 125

Phe Phe Cys Thr Phe Pro Gly His Ser Ala Leu Met Lys Gly Thr Leu
```

```
            130                 135                 140
Thr Leu Lys Arg Gly Asp
145                 150

<210> SEQ ID NO 3
<211> LENGTH: 40
<212> TYPE: DNA
<213> ORGANISM: Artificial Sequence
<220> FEATURE:
<223> OTHER INFORMATION: ssDNA

<400> SEQUENCE: 3
cgcgcgccgc tttagagcgc gcgcgatttc tgcatatata                           40

<210> SEQ ID NO 4
<211> LENGTH: 40
<212> TYPE: DNA
<213> ORGANISM: Artificial Sequence
<220> FEATURE:
<223> OTHER INFORMATION: csDNA

<400> SEQUENCE: 4
tatatatgca gaaatccccc ccctctaaa gcggcgcgcg                            40

<210> SEQ ID NO 5
<211> LENGTH: 21
<212> TYPE: RNA
<213> ORGANISM: Artificial Sequence
<220> FEATURE:
<223> OTHER INFORMATION: siSOX9 antisense

<400> SEQUENCE: 5
aacgagagcg agaagagacc c                                              21

<210> SEQ ID NO 6
<211> LENGTH: 21
<212> TYPE: RNA
<213> ORGANISM: Artificial Sequence
<220> FEATURE:
<223> OTHER INFORMATION: siSOX9 sense

<400> SEQUENCE: 6
gggucucuuc ucgcucucgu u                                              21

<210> SEQ ID NO 7
<211> LENGTH: 447
<212> TYPE: DNA
<213> ORGANISM: Artificial Sequence
<220> FEATURE:
<223> OTHER INFORMATION: original azurin

<400> SEQUENCE: 7
atgctacgta aactcgctgc cgtatccctg ctgtccctgc tcagtgcgcc gctgctggct    60
gccgagtgct cggtggacat ccagggtaac gaccagatgc agttcaacac caatgccatc   120
accgtcgaca agagctgcaa gcagttcacc gtcaacctgt ccaccccgg caacctgccg    180 aagaacgtca tgggccacaa ctgggtactg agcaccgccg ccgacatgca gggcgtggtc   240
accgacggca tggcttccgg cctggacaag gattacctga gcccgacga cagccgcgtc    300 atcgcccaca ccaagctgat cggctcgggc gagaaggact cggtgacctt cgacgtctcc   360
aagctgaagg aaggcgagca gtacatgttc ttctgcacct tcccgggcca ctccgcgctg   420
atgaagggca ccctgaccct gaagtga                                       447
```

```
<210> SEQ ID NO 8
<211> LENGTH: 3
<212> TYPE: PRT
<213> ORGANISM: Artificial Sequence
<220> FEATURE:
<223> OTHER INFORMATION: Synthesized

<400> SEQUENCE: 8

Arg Gly Asp
1

<210> SEQ ID NO 9
<211> LENGTH: 4
<212> TYPE: PRT
<213> ORGANISM: Artificial Sequence
<220> FEATURE:
<223> OTHER INFORMATION: Synthesized

<400> SEQUENCE: 9

Arg Gly Asp Ser
1

<210> SEQ ID NO 10
<211> LENGTH: 4
<212> TYPE: PRT
<213> ORGANISM: Artificial Sequence
<220> FEATURE:
<223> OTHER INFORMATION: Synthesized

<400> SEQUENCE: 10

Arg Gly Asp Cys
1

<210> SEQ ID NO 11
<211> LENGTH: 4
<212> TYPE: PRT
<213> ORGANISM: Artificial Sequence
<220> FEATURE:
<223> OTHER INFORMATION: Synthesized

<400> SEQUENCE: 11

Arg Gly Asp Val
1

<210> SEQ ID NO 12
<211> LENGTH: 4
<212> TYPE: PRT
<213> ORGANISM: Artificial Sequence
<220> FEATURE:
<223> OTHER INFORMATION: Synthesized

<400> SEQUENCE: 12

Arg Gly Glu Ser
1

<210> SEQ ID NO 13
<211> LENGTH: 10
<212> TYPE: PRT
<213> ORGANISM: Artificial Sequence
<220> FEATURE:
<223> OTHER INFORMATION: Synthesized

<400> SEQUENCE: 13

Arg Gly Asp Ser Pro Ala Ser Ser Lys Pro
1               5                   10
```

```
<210> SEQ ID NO 14
<211> LENGTH: 5
<212> TYPE: PRT
<213> ORGANISM: Artificial Sequence
<220> FEATURE:
<223> OTHER INFORMATION: Synthesized

<400> SEQUENCE: 14

Gly Arg Gly Asp Ser
1               5

<210> SEQ ID NO 15
<211> LENGTH: 6
<212> TYPE: PRT
<213> ORGANISM: Artificial Sequence
<220> FEATURE:
<223> OTHER INFORMATION: Synthesized

<400> SEQUENCE: 15

Gly Arg Ala Asp Ser Pro
1               5

<210> SEQ ID NO 16
<211> LENGTH: 4
<212> TYPE: PRT
<213> ORGANISM: Artificial Sequence
<220> FEATURE:
<223> OTHER INFORMATION: Synthesized

<400> SEQUENCE: 16

Lys Gly Asp Ser
1

<210> SEQ ID NO 17
<211> LENGTH: 6
<212> TYPE: PRT
<213> ORGANISM: Artificial Sequence
<220> FEATURE:
<223> OTHER INFORMATION: Synthesized

<400> SEQUENCE: 17

Gly Arg Gly Asp Ser Pro
1               5

<210> SEQ ID NO 18
<211> LENGTH: 6
<212> TYPE: PRT
<213> ORGANISM: Artificial Sequence
<220> FEATURE:
<223> OTHER INFORMATION: Synthesized

<400> SEQUENCE: 18

Gly Arg Gly Asp Thr Pro
1               5

<210> SEQ ID NO 19
<211> LENGTH: 5
<212> TYPE: PRT
<213> ORGANISM: Artificial Sequence
<220> FEATURE:
<223> OTHER INFORMATION: Synthesized

<400> SEQUENCE: 19

Gly Arg Gly Glu Ser
1               5

<210> SEQ ID NO 20
```

```
<211> LENGTH: 7
<212> TYPE: PRT
<213> ORGANISM: Artificial Sequence
<220> FEATURE:
<223> OTHER INFORMATION: Synthesized

<400> SEQUENCE: 20

Gly Arg Gly Asp Ser Pro Cys
1               5

<210> SEQ ID NO 21
<211> LENGTH: 6
<212> TYPE: PRT
<213> ORGANISM: Artificial Sequence
<220> FEATURE:
<223> OTHER INFORMATION: Synthesized

<400> SEQUENCE: 21

Gly Arg Gly Glu Ser Pro
1               5

<210> SEQ ID NO 22
<211> LENGTH: 4
<212> TYPE: PRT
<213> ORGANISM: Artificial Sequence
<220> FEATURE:
<223> OTHER INFORMATION: Synthesized

<400> SEQUENCE: 22

Ser Asp Gly Arg
1

<210> SEQ ID NO 23
<211> LENGTH: 5
<212> TYPE: PRT
<213> ORGANISM: Artificial Sequence
<220> FEATURE:
<223> OTHER INFORMATION: Synthesized

<400> SEQUENCE: 23

Tyr Arg Gly Asp Ser
1               5

<210> SEQ ID NO 24
<211> LENGTH: 15
<212> TYPE: PRT
<213> ORGANISM: Artificial Sequence
<220> FEATURE:
<223> OTHER INFORMATION: Synthesized

<400> SEQUENCE: 24

Gly Gln Gln His His Leu Gly Gly Ala Lys Gln Ala Gly Asp Val
1               5                   10                  15

<210> SEQ ID NO 25
<211> LENGTH: 3
<212> TYPE: PRT
<213> ORGANISM: Artificial Sequence
<220> FEATURE:
<223> OTHER INFORMATION: Synthesized

<400> SEQUENCE: 25

Gly Pro Arg
1

<210> SEQ ID NO 26
<211> LENGTH: 3
```

```
<212> TYPE: PRT
<213> ORGANISM: Artificial Sequence
<220> FEATURE:
<223> OTHER INFORMATION: Synthesized

<400> SEQUENCE: 26

Gly His Lys
1

<210> SEQ ID NO 27
<211> LENGTH: 5
<212> TYPE: PRT
<213> ORGANISM: Artificial Sequence
<220> FEATURE:
<223> OTHER INFORMATION: Synthesized

<400> SEQUENCE: 27

Tyr Ile Gly Ser Arg
1               5

<210> SEQ ID NO 28
<211> LENGTH: 5
<212> TYPE: PRT
<213> ORGANISM: Artificial Sequence
<220> FEATURE:
<223> OTHER INFORMATION: Synthesized

<400> SEQUENCE: 28

Pro Asp Ser Gly Arg
1               5

<210> SEQ ID NO 29
<211> LENGTH: 9
<212> TYPE: PRT
<213> ORGANISM: Artificial Sequence
<220> FEATURE:
<223> OTHER INFORMATION: Synthesized

<400> SEQUENCE: 29

Cys Asp Pro Gly Tyr Ile Gly Ser Arg
1               5

<210> SEQ ID NO 30
<211> LENGTH: 4
<212> TYPE: PRT
<213> ORGANISM: Artificial Sequence
<220> FEATURE:
<223> OTHER INFORMATION: Synthesized

<400> SEQUENCE: 30

Leu Cys Phe Arg
1

<210> SEQ ID NO 31
<211> LENGTH: 3
<212> TYPE: PRT
<213> ORGANISM: Artificial Sequence
<220> FEATURE:
<223> OTHER INFORMATION: Synthesized

<400> SEQUENCE: 31

Glu Ile Leu
1

<210> SEQ ID NO 32
<211> LENGTH: 5
<212> TYPE: PRT
```

```
<213> ORGANISM: Artificial Sequence
<220> FEATURE:
<223> OTHER INFORMATION: Synthesized

<400> SEQUENCE: 32

Glu Ile Leu Asp Val
1               5

<210> SEQ ID NO 33
<211> LENGTH: 8
<212> TYPE: PRT
<213> ORGANISM: Artificial Sequence
<220> FEATURE:
<223> OTHER INFORMATION: Synthesized

<400> SEQUENCE: 33

Glu Ile Leu Asp Val Pro Ser Thr
1               5

<210> SEQ ID NO 34
<211> LENGTH: 8
<212> TYPE: PRT
<213> ORGANISM: Artificial Sequence
<220> FEATURE:
<223> OTHER INFORMATION: Synthesized

<400> SEQUENCE: 34

Glu Ile Leu Glu Val Pro Ser Thr
1               5

<210> SEQ ID NO 35
<211> LENGTH: 3
<212> TYPE: PRT
<213> ORGANISM: Artificial Sequence
<220> FEATURE:
<223> OTHER INFORMATION: Synthesized

<400> SEQUENCE: 35

Leu Asp Val
1

<210> SEQ ID NO 36
<211> LENGTH: 5
<212> TYPE: PRT
<213> ORGANISM: Artificial Sequence
<220> FEATURE:
<223> OTHER INFORMATION: Synthesized

<400> SEQUENCE: 36

Leu Asp Val Pro Ser
1               5

<210> SEQ ID NO 37
<211> LENGTH: 27
<212> TYPE: DNA
<213> ORGANISM: Artificial Sequence
<220> FEATURE:
<223> OTHER INFORMATION: Azu W F

<400> SEQUENCE: 37
catatgctac gtaaactcgc tgccgta                                          27

<210> SEQ ID NO 38
<211> LENGTH: 27
<212> TYPE: DNA
<213> ORGANISM: Artificial Sequence
<220> FEATURE:
```

<223> OTHER INFORMATION: Azu W R

<400> SEQUENCE: 38
gaattcactt cagggtcagg gtgccct                                          27

<210> SEQ ID NO 39
<211> LENGTH: 41
<212> TYPE: DNA
<213> ORGANISM: Artificial Sequence
<220> FEATURE:
<223> OTHER INFORMATION: Azu Cys1 Forward sequence

<400> SEQUENCE: 39
catccagggt aacgaccagt gccagttcaa caccaatgcc a                          41

<210> SEQ ID NO 40
<211> LENGTH: 41
<212> TYPE: DNA
<213> ORGANISM: Artificial Sequence
<220> FEATURE:
<223> OTHER INFORMATION: Azu Cys1 Reverse sequence

<400> SEQUENCE: 40
tggcattggt gttgaactgg cactggtcgt taccctggat g                          41

<210> SEQ ID NO 41
<211> LENGTH: 41
<212> TYPE: DNA
<213> ORGANISM: Artificial Sequence
<220> FEATURE:
<223> OTHER INFORMATION: Azu Cys2 Forward sequence

<400> SEQUENCE: 41
gctgatcggc tcgggcgagt gcgactcggt gaccttcgac g                          41

<210> SEQ ID NO 42
<211> LENGTH: 41
<212> TYPE: DNA
<213> ORGANISM: Artificial Sequence
<220> FEATURE:
<223> OTHER INFORMATION: Azu Cys2 Reverse sequence

<400> SEQUENCE: 42
cgtcgaaggt caccgagtcg cactcgcccg agccgatcag c                          41

<210> SEQ ID NO 43
<211> LENGTH: 41
<212> TYPE: DNA
<213> ORGANISM: Artificial Sequence
<220> FEATURE:
<223> OTHER INFORMATION: Azu Cys3 Forward sequence

<400> SEQUENCE: 43
cctgtcccac cccggcaact gcccgaagaa cgtcatgggc c                          41

<210> SEQ ID NO 44
<211> LENGTH: 41
<212> TYPE: DNA
<213> ORGANISM: Artificial Sequence
<220> FEATURE:
<223> OTHER INFORMATION: Azu Cys3 Reverse sequence

<400> SEQUENCE: 44
ggcccatgac gttcttcggg cagttgccgg ggtgggacag g                          41

<210> SEQ ID NO 45
<211> LENGTH: 69
<212> TYPE: DNA
<213> ORGANISM: Artificial Sequence
<220> FEATURE:
<223> OTHER INFORMATION: Azu RGD Forward sequence

<400> SEQUENCE: 45
gcgctgatga agggcaccct gaccctgaag cgcggggatt gaggatccgg ctgctaacaa    60
agcccgaaa                                                            69

<210> SEQ ID NO 46
<211> LENGTH: 69
<212> TYPE: DNA
<213> ORGANISM: Artificial Sequence
<220> FEATURE:
<223> OTHER INFORMATION: Azu RGD Reverse sequence

<400> SEQUENCE: 46
tttcgggctt tgttagcagc cggatcctca atccccgcgc ttcagggtca gggtgccctt    60
catcagcgc                                                            69

<210> SEQ ID NO 47
<211> LENGTH: 25
<212> TYPE: DNA
<213> ORGANISM: Artificial Sequence
<220> FEATURE:
<223> OTHER INFORMATION: ssDNA 2

<400> SEQUENCE: 47
ataaaaaaaa cgcgggggtt ccgcg                                          25

<210> SEQ ID NO 48
<211> LENGTH: 25
<212> TYPE: DNA
<213> ORGANISM: Artificial Sequence
<220> FEATURE:
<223> OTHER INFORMATION: csDNA 2

<400> SEQUENCE: 48
gcgcccccaa ggcgcaaaaa taaaa                                          25

<210> SEQ ID NO 49
<211> LENGTH: 13
<212> TYPE: PRT
<213> ORGANISM: Artificial Sequence
<220> FEATURE:
<223> OTHER INFORMATION: CPP (CTAT)

<400> SEQUENCE: 49

Cys Gly Arg Lys Lys Arg Arg Gln Arg Arg Pro Gln
1               5                   10

<210> SEQ ID NO 50
<211> LENGTH: 3
<212> TYPE: PRT
<213> ORGANISM: Artificial Sequence
<220> FEATURE:
<223> OTHER INFORMATION: Peptide 1

<400> SEQUENCE: 50

Thr Gly Gly
1

<210> SEQ ID NO 51

```
<211> LENGTH: 4
<212> TYPE: PRT
<213> ORGANISM: Artificial Sequence
<220> FEATURE:
<223> OTHER INFORMATION: Peptide 2

<400> SEQUENCE: 51

Trp Gly Gly Cys
1

<210> SEQ ID NO 52
<211> LENGTH: 21
<212> TYPE: DNA
<213> ORGANISM: Artificial Sequence
<220> FEATURE:
<223> OTHER INFORMATION: Oct 4 Forward sequence

<400> SEQUENCE: 52
gaggctacag ggacaccttt c                                           21

<210> SEQ ID NO 53
<211> LENGTH: 18
<212> TYPE: DNA
<213> ORGANISM: Artificial Sequence
<220> FEATURE:
<223> OTHER INFORMATION: Oct 4 Reverse sequence

<400> SEQUENCE: 53
gtgccaaagt ggggacct                                               18

<210> SEQ ID NO 54
<211> LENGTH: 24
<212> TYPE: DNA
<213> ORGANISM: Artificial Sequence
<220> FEATURE:
<223> OTHER INFORMATION: NANOG Forward sequence

<400> SEQUENCE: 54
aaattggtga tgaagatgta ttcg                                        24

<210> SEQ ID NO 55
<211> LENGTH: 20
<212> TYPE: DNA
<213> ORGANISM: Artificial Sequence
<220> FEATURE:
<223> OTHER INFORMATION: NANOG Reverse sequence

<400> SEQUENCE: 55
gcaaaacaga gccaaaaacg                                             20

<210> SEQ ID NO 56
<211> LENGTH: 24
<212> TYPE: DNA
<213> ORGANISM: Artificial Sequence
<220> FEATURE:
<223> OTHER INFORMATION: SOX2 Forward sequence

<400> SEQUENCE: 56
ttcacatgtc ccagcactac caga                                        24

<210> SEQ ID NO 57
<211> LENGTH: 26
<212> TYPE: DNA
<213> ORGANISM: Artificial Sequence
<220> FEATURE:
<223> OTHER INFORMATION: SOX2 Reverse sequence
```

```
<400> SEQUENCE: 57
tcacatgtgt gagaggggca gtgtgc                                      26

<210> SEQ ID NO 58
<211> LENGTH: 20
<212> TYPE: DNA
<213> ORGANISM: Artificial Sequence
<220> FEATURE:
<223> OTHER INFORMATION: PAX6 Forward sequence

<400> SEQUENCE: 58
tgtccaacgg atgtgtgagt                                             20

<210> SEQ ID NO 59
<211> LENGTH: 20
<212> TYPE: DNA
<213> ORGANISM: Artificial Sequence
<220> FEATURE:
<223> OTHER INFORMATION: PAX6 Reverse sequence

<400> SEQUENCE: 59
tttcccaagc aaagatggac                                             20

<210> SEQ ID NO 60
<211> LENGTH: 18
<212> TYPE: DNA
<213> ORGANISM: Artificial Sequence
<220> FEATURE:
<223> OTHER INFORMATION: Ngn2 Forward sequence

<400> SEQUENCE: 60
acatctggag ccgcgtag                                               18

<210> SEQ ID NO 61
<211> LENGTH: 22
<212> TYPE: DNA
<213> ORGANISM: Artificial Sequence
<220> FEATURE:
<223> OTHER INFORMATION: Ngn2 Reverse sequence

<400> SEQUENCE: 61
cagcagcatc agtacctcct ct                                          22

<210> SEQ ID NO 62
<211> LENGTH: 21
<212> TYPE: DNA
<213> ORGANISM: Artificial Sequence
<220> FEATURE:
<223> OTHER INFORMATION: Math2 Forward sequence

<400> SEQUENCE: 62
cgacactcag cctgaaaaga t                                           21

<210> SEQ ID NO 63
<211> LENGTH: 21
<212> TYPE: DNA
<213> ORGANISM: Artificial Sequence
<220> FEATURE:
<223> OTHER INFORMATION: Math2 Reverse sequence

<400> SEQUENCE: 63
caaactttct gcacatctgg g                                           21

<210> SEQ ID NO 64
<211> LENGTH: 20
```

```
<212> TYPE: DNA
<213> ORGANISM: Artificial Sequence
<220> FEATURE:
<223> OTHER INFORMATION: ACTB Forward sequence

<400> SEQUENCE: 64
gtcctctccc aagtccacac                                              20

<210> SEQ ID NO 65
<211> LENGTH: 20
<212> TYPE: DNA
<213> ORGANISM: Artificial Sequence
<220> FEATURE:
<223> OTHER INFORMATION: ACTB Reverse sequence

<400> SEQUENCE: 65
gggagaccaa aagccttcat                                              20

<210> SEQ ID NO 66
<211> LENGTH: 4
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (4)..(4)
<223> OTHER INFORMATION: Xaa can be any naturally occurring amino acid

<400> SEQUENCE: 66

Trp Gly Gly Xaa
1

<210> SEQ ID NO 67
<211> LENGTH: 5
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (4)..(5)
<223> OTHER INFORMATION: Xaa can be any naturally occurring amino acid

<400> SEQUENCE: 67

Trp Gly Gly Xaa Xaa
1               5

<210> SEQ ID NO 68
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (4)..(6)
<223> OTHER INFORMATION: Xaa can be any naturally occurring amino acid

<400> SEQUENCE: 68

Trp Gly Gly Xaa Xaa Xaa
1               5
```

BIOMOLETRON FOR REGULATION STEM CELL DIFFERENTIATION

FIELD

This application claims priority to and the benefit of Korean Patent Application No. 10-2016-0032252 filed in the Korean Intellectual Property Office on 17 Mar. 2016, the disclosure of which is incorporated herein by reference.

The present invention relates to a biomoletron for controlling neural stem cell differentiation and, more specifically, to a biomoletron device composed of a biomolecule (recombinant protein)/an organic material (DNA nucleotide pair combined with metal ions)/an inorganic material (nanoparticle complex).

BACKGROUND

Cell control technology has received great attention as a next-generation technology essential in various research fields, such as cell-based biosensors, drug screening, and stem cell differentiation. Particularly, the selective control of differentiation at the cellular level is an essential technique in conducting research in the fields of stem cell therapy and regenerative medicine.

Although various techniques have been developed to control the differentiation of neural stem cells, the control of differentiation at the cellular level is limited. Electrical stimulation-based differentiation induction techniques can kill cells through voltage-induced cell damage and excessive free radical generation; differentiation-inducing factor (DIF)-based induction techniques, which are on the basis of cells in a bulk state, have limits in efficient delivery of DIF to cells; and cell culture environment-based induction techniques have limits in the induction of differentiation in a selective direction. In addition, free radicals generated during the stem cell differentiation process have a great influence on the stability of differentiation, and thus direct control of free radicals is needed for efficient control of differentiation. Therefore, a new approach capable of effectively controlling the differentiation of neural stem cells at the cellular level is needed.

Throughout the specification, many papers and patent documents are used as references, and the citations thereof are represented. The disclosure of the cited papers and patent documents is incorporated in the present specification by reference in its entirety, to describe a level of a technical field to which the present invention pertains and content of the present invention more clearly.

PRIOR ART DOCUMENTS

Non-Patent Documents (Non-Patent Document 1) K.-A. Chang, et al., PLoS ONE, 6, e18738 (2011)

(Non-Patent Document 2) Y.-J. Huang, et al., Small, 8, 2869 (2012)

(Non-Patent Document 3) J. T. Robinson, et al., Nature Nanotechnology, 7, 180 (2012)

(Non-Patent Document 4) C. Liu, et al., Nano Letters, 13, 2989 (2013)

(Non-Patent Document 5) O. Yanes, et al., Nature chemical biology, 6, 411 (2010)

(Non-Patent Document 6) K. Wang, et al., Cell death and disease, 4, e537 (2013)

(Non-Patent Document 7) Y. Yan, et al., Cell, 138, 1209 (2009)

DETAILED DESCRIPTION

The present inventors endeavored to develop bioelectronic devices that can precisely control cell differentiation at the single-cell level. As a result, the present inventors developed a novel concept of biomoletron, which is composed of: a biomolecule (recombinant protein having a redox potential), which is integrated with the cell membrane to release a cell differentiation-inducing factor to thereby promote the differentiation of cells; an organic material (double strand DNA combined with metal ions); and an inorganic material (nanoparticle complex), and confirmed a cell differentiation control potential and a free radical inhibition potential thereof, and thus completed the present invention.

Accordingly, an aspect of the present invention is to provide a bioelectronic device for controlling cell differentiation.

Another aspect of the present invention is to provide a method for promoting cell differentiation.

Still another aspect of the present invention is to provide a method for manufacturing a bioelectronic device for controlling cell differentiation.

Other purposes and advantages of the present disclosure will become more obvious with the following detailed description of the invention, claims, and drawings.

In accordance with an aspect of the present invention, there is provided a bioelectronic device for controlling stem cell differentiation, including:

(a) a protein having a redox potential;

(b) a first single strand DNA binding to the N-terminal of the protein having a redox potential;

(c) a second single strand DNA complimentarily hybridizing with the first single strand DNA to form a double strand DNA;

(d) a nanoparticle directly conjugated to a terminal of the second single strand DNA; and (e) (i) a cell-penetrating peptide and (ii) a differentiation-inducing factor, which are conjugated to the nanoparticle.

The present inventors endeavored to develop bioelectronic devices that can precisely control cell differentiation at the single-cell level. As a result, the present inventors developed a novel concept of biomoletron, which is composed of: a biomolecule (recombinant protein having a redox potential), which is integrated with the cell membrane to release a cell differentiation-inducing factor to thereby promote the differentiation of cells; an organic material (double strand DNA combined with metal ions); and an inorganic material (nanoparticle complex), and confirmed a cell differentiation control potential and a free radical inhibition potential thereof.

The bioelectronic device for controlling stem cell differentiation of the present invention can be applied to various stem cells.

According to an embodiment of the present invention, the stem cells of the present invention are totipotent stem cells, pluripotent stem cells, multipotent stem cells, or unipotent stem cells.

According to another embodiment of the present invention, the multipotent stem cells of the present invention are neural stem cells, hematopoietic stem cells, or mesenchymal stem cells.

According to a particular embodiment of the present invention, the stem cells of the present invention are neural stem cells.

As used herein, the term "stem cells" is a generic term for undifferentiated cells before differentiation into respective cells constituting tissues, and the stem cells have a potential to differentiate into particular cells by particular differentiation stimulations (environments). Stem cells, unlike cell division-ceased undifferentiated cells, are capable of producing the same cells as their own through cell division (self-renewal), and have plasticity in differentiation, in which the stem cells differentiate into particular cells by application of the differentiation stimulation and may differentiate into various cells by different environments or by different differentiation stimulations.

As used herein, the term "bioelectronic device" refers to a device in which biomolecules are designed and combined such that one biomolecule functions as an element of an electronic device through the application of a diversity of biological functions and integrated through molecular wiring. The bioelectronic device is designed to overcome physical limitations of semiconductors. The bioelectronic device has various advantages in terms of nanotechnology for designing, assembling, and fabricating devices from molecular-unit ultrafine structures. When compared with existing semiconductor devices in which wirings were formed on silicon using conventional photolithography, molecular electronic devices using biomolecules have the following advantages: First, biomolecules having a size of several tens of angstroms (Å) to several nanometers (nm) are used, so integration density can be improved by more than 10 million times that of existing silicon chips, and such integration allows more information to be stored in a smaller space and enables a high-density integration due to very little heat generation. Second, microprocessing can be achieved and manufacturing costs are reduced by the self-assembly and orientation of biomolecules. Third, parallel signal processing used in nervous systems can be achieved. Fourth, the intermolecular information transmission is performed, so information transmission rates can be improved and errors in information exchange can be reduced, and information transmission rates can be improved by not only using information transmission by electrons but also applying light as an information transmission means.

The bioelectronic device for controlling stem cell differentiation of the present invention will be described in detail by elements.

(a) Protein Having Redox Potential

The protein having a redox potential, constituting the bioelectronic device of the present invention, can be any protein having a redox potential known in the art.

According to an embodiment of the present invention, the protein having a redox potential is azurin, hemoglobin, myoglobin, hemerythrin, hemochromogen, cytochrome, iron-sulfur protein, rubredoxin, plastocyanin, ferritin, ceruloplasmin, carbonic anhydrase, vitamin B12-dependent enzyme, nitrogenase, superoxide dismutase, chlorophyll-containing protein, calmodulin, glucose-6-phosphatase, hexokinase, DNA polymerase, vanabin, arginase, catalase, hydrogenases, iron-responsive element binding protein, aconitase, urease, cytochrome oxidase, laccase, alcohol dehydrogenase, carboxy peptidase, amino peptides, β-amyloid protein, nitrate reductase, glutathione peroxidase, metallothionein, or phosphatase.

According to another embodiment of the present invention, the protein having a redox potential is azurin.

The present inventors introduced cysteine residues into the azurin such that the azurin was self-assembled on a substrate.

According to an embodiment of the present invention, the protein having a redox potential is directly immobilized to the substrate by having cysteine residues introduced thereto.

According to another embodiment of the present invention, the protein having a redox potential is directly immobilized to the substrate by having 2 to 10 cysteine residues introduced thereto.

According to a particular embodiment of the present invention, the protein having a redox potential is directly immobilized to the substrate by having 2 to 5 cysteine residues introduced thereto.

As validated in the examples below, the protein having a redox potential is directly and stably immobilized to a substrate by having three cysteine residues introduced thereinto.

According to an embodiment of the present invention, the substrate may be made of a metal, a metal oxide, glass, ceramic, quartz, silicon, a semiconductor, a Si/SiO$_2$ wafer, germanium, gallium arsenide, carbon, carbon nanotubes, a polymer, Sepharose, or agarose.

According to another embodiment of the present invention, the substrate is a metal substrate. According to a particular embodiment of the present invention, the substrate is a gold (Au) substrate.

The bioelectronic device of the present invention includes a substrate for an electric device when the bioelectronic device of the present invention is electrically operated. The substrate is as described above, and in the examples below, the substrate is an electrically charged substrate having a gold coated surface. A redox-active layer is formed on the substrate. In the present invention, a protein having a redox potential, which is self-assembled on the substrate through cysteine introduction, is used as the redox-active layer. The redox-active layer is in a predetermined electronic state, for example, an oxidation state or a reduction state, by the protein having a redox potential.

The present inventors introduced cysteine residues into the protein having a redox potential through the induction of site-directed mutagenesis.

According to an embodiment of the present invention, the protein having a redox potential includes the amino acid sequence of SEQ ID NO: 2.

According to another embodiment of the present invention, the protein having a redox potential includes the nucleotide sequence of SEQ ID NO: 1.

As validated in the example below, the protein having a redox potential is directly immobilized to a substrate through substituted cysteine residues in which the 13th amino acid methionine is cysteine (Met13Cys); the 92nd amino acid lysine is substituted with cysteine (Lys92Cys); and the 39th amino acid leucine is substituted with cysteine (Leu39Cys).

The introduced cysteine residues are allowed to form a stable single film with excellent orientation on a substrate, preferably a metal substrate, more preferably a gold (Au) substrate. According to a preferable embodiment of the present invention, the number of cysteine residues introduced to the recombinant protein is 2 to 10. If the number of introduced cysteine residues is smaller than 2, that is, 1, the function of the cysteine residue as an anchoring site is significantly decreased. If the number of cysteine residues is greater than 10, disulfide bonds are formed between the introduced cysteine residues, so that not only is the recombinant protein difficult to purify, but the function of cysteine residues as an anchoring site is significantly decreased.

The protein immobilization through thiol groups of the introduced cysteine residues is expressed by direct immobilization in the present specification. As used herein, the term "direct immobilization" means a direct immobilization of a protein to a substrate through a molecule in the protein without the help of any other linker.

Through such direct immobilization, resistance layers unnecessary in the electron transfer process can be reduced and the immobilization potential can also be maximized under a given condition.

As a technique for immobilizing a protein on a substrate, a linker is currently used most frequently. However, such a technique has disadvantages in that (i) it requires too much processing, (ii) it exhibits a low immobilization rate, and (iii) it causes an insulating effect of the linker layer.

These problems of the prior art can be solved by using direct immobilization of the present invention.

The protein having a redox potential constituting the bioelectronic device of the present invention is a metalloprotein that contains a metal ion.

The metal ion of the metalloprotein used in the present invention is magnesium ion, vanadium ion, manganese ion, iron ion, nickel ion, copper ion, zinc ion, molybdenum ion, cobalt ion, gallium ion, bismuth ion, gold ion, aluminum ion, platinum ion, chromium ion, silver ion, antimony ion, thallium ion, cadmium ion, mercury ion, lead ion, calcium ion, or selenium ion.

According to an embodiment of the present invention, the protein having a redox potential includes a copper ion.

The protein having a redox potential constituting the bioelectronic device of the present invention further contains a ligand, which has a binding ability to a cell membrane receptor protein.

According to an embodiment of the present invention, the protein having a redox potential further contains a ligand, which has a binding ability to a cell membrane receptor protein, at the C-terminal thereof.

According to another embodiment of the present invention, the ligand having a binding ability to a cell membrane receptor protein is at least one ligand selected from the group consisting of RGD(SEQ ID NO: 8), RGDS(SEQ ID NO: 9), RGDC(SEQ ID NO: 10), RGDV(SEQ ID NO: 11), RGES (SEQ ID NO: 12), RGDSPASSKP(SEQ ID NO: 13), GRGDS(SEQ ID NO: 14), GRADSP(SEQ ID NO: 15), KGDS(SEQ ID NO: 16), GRGDSP(SEQ ID NO: 17), GRGDTP(SEQ ID NO: 18), GRGES(SEQ ID NO: 19), GRGDSPC(SEQ ID NO: 20), GRGESP(SEQ ID NO: 21), SDGR(SEQ ID NO: 22), YRGDS(SEQ ID NO: 23), GQQHHLGGAKQAGDV SEQ ID NO: 24), GPR(SEQ ID NO: 25), GHK(SEQ ID NO: 26), YIGSR(SEQ ID NO: 27), PDSGR(SEQ ID NO: 28), CDPGYIGSR(SEQ ID NO: 29), LCFR(SEQ ID NO: 30), EIL(SEQ ID NO: 31), EILDV (SEQ ID NO: 32),EILDVPST(SEQ ID NO: 33), EILEVPST (SEQ ID NO: 34), LDV(SEQ ID NO: 35), and LDVPS(SEQ ID NO: 36).

According to another embodiment of the present invention, the ligand having a binding ability to a cell membrane receptor protein is RGD (SEQ ID NO: 8), RGDS(SEQ ID NO: 9), RGDC(SEQ ID NO: 10), RGDV(SEQ ID NO: 11), RGES(SEQ ID NO: 12), or RGDSPASSKP(SEQ ID NO: 13).

According to a particular embodiment of the present invention, the ligand having a binding ability to a cell membrane receptor protein is RGD (SEQ ID NO: 8).

In the bioelectronic device of the present invention, the protein having a redox potential is combined to cell membranes by introducing RGD into the C-terminal thereof.

The bioelectronic device of the present invention has a free radical-scavenging potential, together with a stem cell differentiation controlling potential.

According to an embodiment of the present invention, the protein having a redox potential includes a free radical-scavenging potential.

As validated in the examples below, the protein having a redox potential has a function of scavenging hydrogen peroxide as one of reactive oxygen species.

The free radicals generated during the stem cell differentiation process have a great influence on the stability of differentiation, and thus the direct control thereof is needed for efficient control of differentiation. The bioelectronic device of the present invention scavenges free radicals to improve stability of differentiation in controlling stem cell differentiation.

(b) First Single Strand DNA

The bioelectronic device for controlling stem cell differentiation of the present invention includes a first single strand DNA binding to the N-terminal of the protein having a redox potential.

According to an embodiment of the present invention, the first single strand DNA is 10-100 bp in length.

According to another embodiment of the present invention, the first single strand DNA is 10-80 bp, 10-60 bp, 10-50 bp, 20-50 bp, or 30-50 bp in length.

As used herein, the term "single strand DNA" refers to a linear oligomer of natural or modified monomers or linkages, and the single strand DNA includes a deoxyribonucleotide, can specifically hybridize with a target nucleotide sequence, and exists naturally or is artificially synthesized. The single strand DNA of the present invention may include naturally occurring dNMPs (i.e., dAMP, dGMP, dCMP, and dTMP), or nucleotide analogs or derivatives.

According to an embodiment of the present invention, the first single strand DNA includes the nucleotide sequence of SEQ ID NO: 3.

The first single strand DNA indirectly binds to the N-terminal of the protein having a redox potential through a linker.

The linker of the present invention includes any linker in the art, which can bind a protein and DNA to each other.

According to an embodiment of the present invention, the linker is sulfosuccinimidyl-4-(maleimidomethyl)cyclohexane-1-carboxylate (SMCC), formaldehyde, 1-ethyl-3-[3-dimethylaminopropyl]carbodiimide hydrochloride (EDC), bis[beta-(4-azidosalicylamido)ethyl]disulfide) (BASED), or bis-maleimidohexane (BMH).

According to a certain embodiment of the present invention, the linker is SMCC.

The hybrid of the present invention may be prepared by the following various methods:

(i) An amino group of the protein having a redox potential reacts with a linker (e.g., sulfo-SMCC) to form an amide bond, and then thiol-modified ssDNA (sulfhydryl-containing biomolecule) is added to react with a maleimide group of the recombinant azurin-linker to form a thioester bond, thereby preparing a recombinant azurin-ssDNA hybrid.

(ii) Thiol-modified ssDNA (sulfhydryl-containing biomolecule) reacts with a linker. The protein having a redox potential is added to the thiol-modified ssDNA linker to form an amine bond, thereby preparing a protein having a redox potential-ssDNA hybrid.

(iii) The amine-modified ssDNA reacts with a linker to form an amide bond. The protein having a redox potential is treated with DDT to reduce cysteine resides of azurin molecule, thereby preparing a protein having a redox potential. The protein having a redox potential reacts with the amine-modified ssDNA-linker to form a thioester bond, thereby preparing a protein having a redox potential-ssDNA hybrid.

(iv) The protein having a redox potential is treated with DDT to reduce cysteine residue of protein molecule. The protein having a redox potential reacts with a linker to form a thioester bond. The amine-modified ssDNA is added to prepare a protein having a redox potential-ssDNA hybrid.

As validated in the example below, the first single strand DNA of the present invention indirectly binds to the protein having a redox potential through method (ii) above.

(c) Second Single Strand DNA

A second single strand DNA complimentarily hybridizes with the first single strand DNA to form a double strand DNA.

According to an embodiment of the present invention, the second single strand DNA is 10-100 bp in length. According to another embodiment of the present invention, the second single strand DNA is 10-80 bp, 10-60 bp, 10-50 bp, 20-50 bp, or 30-50 bp in length.

The second single strand DNA has a sequence that is partially complementary to the first single strand DNA.

As used herein, the term "complementary" means being sufficiently complementary such that the second single strand DNA selectively hybridizes with the first single strand DNA under certain annealing conditions or strict conditions. The term is meant to encompass "substantially complementary" and "perfectly complementary", and preferably means being perfectly complementary.

The second single strand DNA, together with the first single strand DNA, includes mismatch nucleotide pairs.

As used herein, the term "mismatch" means that a nucleotide to be originally paired makes a pair with a different nucleotide. For example, a nucleotide pair of guanine and guanine but not a nucleotide pair of cytosine and guanine is a mismatch nucleotide pair.

According to an embodiment of the present invention, the number of mismatch nucleotide pairs is 1 to 10.

According to another embodiment of the present invention, the number of mismatch nucleotide pairs is 1 to 8, 1 to 6, or 2 to 6.

According to an embodiment of the present invention, the second single strand DNA includes the nucleotide sequence of SEQ ID NO: 4.

The second single strand DNA hybridizes with the first single strand DNA.

As used herein, the term "hybridization" means that complementary single strand nucleic acids form a double strand nucleic acids. The hybridization may occur when complementarity between two stands of nucleic acids is perfectly matched or even when some mismatch nucleotides are present. The degree of complementarity required for hybridization may vary depending on the hybridization conditions, and may be controlled by, particularly, the temperature.

Metal ions may be further provided between mismatch nucleotide pairs of a double strand NDA obtained by hybridization of the first single strand DNA and the second single strand DNA.

The metal ions are introduced in order to increase the conductivity of DNA.

According to an embodiment of the present invention, the metal ions are positively charged metal ions. For example, silver (Ag+) ion, mercury ion (Hg2+), or the like may be used.

According to another embodiment of the present invention, the metal ion is a silver (Ag) ion.

The second single strand DNA is directly conjugated to the second single strand DNA through a thiol group introduced to a terminal thereof.

(d) Nanoparticle

A nanoparticle is directly conjugated to the terminal of the second single strand DNA.

The nanoparticle is directly conjugated through the thiol group introduced into the terminal of the second single strand DNA.

The nanoparticle constituting the bioelectronic device of the present invention can be any nanoparticle.

According to an embodiment of the present invention, the nanoparticle is a metal nanoparticle, a metal oxide nanoparticle, or an alloy nanoparticle, and a semiconductor nanoparticle.

According to another embodiment of the present invention, the nanoparticle is a metal nanoparticle.

According to a particular embodiment, the nanoparticle is a gold (Au) nanoparticle.

The size of the nanoparticle can be any size with which the nanoparticle can be uptaken into cells [M. K. Hossain, et al., Biosensors and Bioelectronics, 71, 300 (2015)].

According to an embodiment of the present invention, the nanoparticle is 1-20 nm in size.

According to another embodiment of the present invention, the nanoparticle is 1-15 nm in size.

According to a particular embodiment of the present invention, the nanoparticle is 1-10 nm in size.

(e) Cell-Penetrating Peptide and Differentiation-Inducing Factor

A cell-penetrating peptide and a differentiation-inducing factor are conjugated to the nanoparticle.

As used herein, the term "cell-penetrating peptide" refers to a peptide that penetrates a cell membrane to enter a cell, and the cell-penetrating peptide is effectively taken into the cell without applying toxicity to the cell, using energy, and passing through a particular cell membrane receptor. Most cell-penetrating peptides are usually composed of 10-30 amino acids in short length, and most contain a lot of basic amino acids and some show an amphipathic alpha-helical structure.

The cell-penetrating peptide may be any known peptide that has cell-penetrating ability. Examples of the cell-penetrating peptide include Tat, antennapedia, penetratin, transportan, VP22, Hph-1, R11(R9), signal sequence based peptides, and amphipathic peptides, and the like.

According to an embodiment of the present invention, the cell-penetrating peptide is Tat.

For direct immobilization of the cell-penetrating peptide to the nanoparticle, cysteine is introduced into the cell-penetrating peptide. The cell-penetrating peptide is conjugated to a surface of the nanoparticle through a thiol group of the introduced cysteine.

The differentiation-inducing factor is indirectly conjugated to the nanoparticle through a linker, Cucibit [8] Uril (CB), and a peptide, which is introduced to the surface of the nanoparticle.

The linker, Cucibit [8] Uril (CB), and peptide form a complex by a self-assembly method [Feng Tian et al., Langmuir, 27, 4, (2011)].

The linker is a linker having thiol groups at both sides thereof.

According to an embodiment of the present invention, the linker is 5,5'-bis(mercaptomethyl)-2,2'-bipyridine, 1,2-ethandithiol, 1,3-propanedithiol, 1,4-butanedithiol, 2,3-butanedithiol, 1,5-pentanedithiol, 1,6-hexanedithiol, 1,8-octanedithiol, 1,9-nonanedithiol, tetra(ethylene glycol) dithiol, hexa(ethylene glycol) dithiol, or 2,2'-(ethylenedioxy)diethanethiol.

The peptide connects the linker and the differentiation-inducing factor, and is released together with the differentiation-inducing factor upon application of a potential.

The peptide can be any peptide in which the first to third amino acid sequences are WGG (Trp-Gly-Gly). For example, the peptide is TrpGlyGlyXaa(SEQ ID NO: 66), TrpGlyGlyXaaXaa(SEQ ID NO: 67), or TrpGlyGlyXaaXaaXaa (SEQ ID NO: 68). Here, Xaa means any amino acid.

According to an embodiment of the present invention, the peptide is WGG (Trp-Gly-Gly).

For the indirect connection of the peptide and the differentiation-inducing factor, an additional functional group may be added.

As validated in the examples below, the retinoic acid directly binds to the N-terminal of the WGG peptide, and siSOX9 binds to a thiol group of cysteine introduced into the N-terminal of the WGG peptide and a maleimide group introduced into siSOX9.

The differentiation-inducing factor indirectly conjugated to the nanoparticle in the present invention can be any differentiation-inducing factor that is used in the differentiation of stem cells known in the art. Examples of the differentiation-inducing factor include siRNA, shRNA, miRNA, ribozyme, DNAzyme, peptide nucleic acid (PNA), antisense oligonucleotide, peptide, antibody, and aptamer.

According to an embodiment of the present invention, the differentiation-inducing factor is at least one differentiation-inducing factor selected from the group consisting of retinoic acid, siSOX9, brain-derived neurotrophic factor (BDNF), glial cell-derived neurotrophic factor (GDNF), valproic acid, ciliary neurotrophic factor (CNTF), platelet-derived growth factor (PDGF), sonic hedgehog (SHH), insulin-like growth factor 1 (IGF-1), fibroblast growth factor 4 (FGF-4), bone morphogenetic protein 2 (BMP-2), and dibutyryl-cAMP.

According to an embodiment of the present invention, the differentiation-inducing factor is retinoic acid or siSOX9.

According to another embodiment of the present invention, the siSOX9 includes the nucleotides sequence of SEQ ID NO: 5 and the nucleotides sequence of SEQ ID NO: 6.

As validated in the example below, the application of a potential of −0.5 V to the bioelectronic device of the present invention results in the release of RA and siSOX9 antisense or siSOX9 sense, which is indirectly conjugated to the surface of the nanoparticle. As for RA and siSOX9, the three substances 5,5'-bis(mercaptomethyl)-2,2'-bipyridine, Cucibit [8] Uril (CB), and WGG(Trp-Gly-Gly) peptide are connected to each other, and then upon application of a potential, only the WGG(Trp-Gly-Gly) peptide, which has been attached to the two differentiation-inducing substances, is released.

The bioelectronic device of the present invention is taken into stem cells, and releases the differentiation-inducing factor according to the potential application, thereby inducing the differentiation of stem cells.

According to an embodiment of the present invention, the bioelectronic device is integrated into a cell membrane by a ligand having a binding ability to a cell membrane receptor protein, the ligand being introduced to the C-terminal of the recombinant azurin.

The present invention is directed to an information storage device capable of changing the redox state of the immobilized protein by electrochemically controlling an applied voltage. A substrate having a protein thin film formed thereon is placed in an electrolytic solution, for example, a HEPES electrolyte. The substrate is a working electrode, and connected to a potentiostat to be operated, and a reference electrode (e.g., Ag/AgCl) and a counter electrode (e.g., Pt) are inserted in the electrolyte. The reference electrode is used as a reference for reading a potential change of the working electrode when the potentiostat sweeps the voltage. The counter electrode is used as a passage through which electrons flow by the control of a potential of the potentiostat. Such a 3-electrode system has been known as one of the systems that are most configured in electrochemistry. A simple voltage-current curve is obtained from the simple electrochemical system through cyclic voltammetry.

According to another aspect of the present invention, the present invention provides a method for controlling stem cell differentiation, the method including a step for contacting the bioelectronic device with stem cells.

As validated in the examples below, the differentiation of stem cells is controlled by incubating stem cells in a cell incubator (e.g., chamber), in which the bioelectronic devices are immobilized, and then applying a potential thereto.

According to an embodiment of the present invention, the potential is −4.0 V to−0.1 V.

According to another embodiment of the present invention, the potential is −3.0 V to−0.1 V.

According to a particular embodiment of the present invention, the potential is −2.0 V to−0.1 V.

As validated in the examples below, the potential is applied to a cell incubator, in which the bioelectronic devices are immobilized, for a predetermined time.

According to an embodiment of the present invention, the potential application time is 10-100 seconds.

According to another embodiment of the present invention, the potential application time is 10-800 seconds, 10-600 seconds, 10-400 seconds, 10-300 seconds, or 50-300 seconds.

According to still another embodiment of the present invention, the present invention provides a method for fabricating a bioelectronic device for controlling stem cell differentiation.

The method for controlling stem cell differentiation and the method for fabricating a bioelectronic device for controlling stem cell differentiation of the present invention use the bioelectronic device, and thus the description of overlapping contents therebetween is omitted to avoid excessive complication of the present specification.

Features and advantages of the present invention are summarized as follows.

(a) The present invention provides a bioelectronic device for controlling stem cell differentiation, a method for differentiation of stem cells using the same, and a method for fabricating the bioelectronic device.

(b) The present invention provides a bioelectronic device capable of effectively controlling stem cell differentiation at the single-cell level.

(c) The bioelectronic device of the present invention can perform not only the control of stem cell differentiation but also a free radical inhibiting function.

BRIEF DESCRIPTION OF THE DRAWINGS

FIG. 8A is a cyclic voltammetry graph before and after electric release.

FIG. 8B shows fluorescence images before and after electric release.

FIG. 10A shows the results of investigating and confirming a surface of a biomoletron using surface plasmon resonance before application of a potential (e) and after application of a potential of −0.5 V (f) and a potential of −1.0 V (g).

FIG. 10B is a graph using amperometric measurement upon application of a potential of −0.5 V.

FIG. 10C is a graph using amperometric measurement upon application of a potential of −1.0 V.

FIG. 11a shows fluorescence images to confirm that a biomolecule was fabricated near a cell membrane, using a confocal microscope.

FIG. 11B shows fluorescence images excluding a case of "no penetrating into cell membrane".

FIG. 11C shows fluorescence images excluding a case of "whole penetrating into cell membrane".

FIG. 12a shows the results of confirming the differentiation of neural stem cells using immunostaining.

FIG. 12B shows the results of confirming the differentiation using detection quantitative PCR.

Hereinafter, the present invention will be described in detail with reference to examples. These examples are only for illustrating the present invention more specifically, and it will be apparent to those skilled in the art that the scope of the present invention is not limited by these examples.

EXAMPLES

Materials and Method

Materials

Azu W, Azu Cys1, Azu Cys2, Azu Cys3, Azu RGD primer pairs were purchased from Integrated DNA Technologies (USA). All chemical products (hydrogen peroxide ($H_2O_2$), sulfuric acid ($H_2SO_4$), ammonium hydroxide ($NH_4OH$), silver nitrate ($AgNO_3$)) were purchased from Sigma Aldrich (USA) and PDMS (poly-dimethylsiloxane) was purchased from Corning (USA). Reagent grades of isopropyl alcohol, anhydrous alcohol, distilled water, and phosphoric acid were used, and aluminum foil was purchased from Alpha (Korea). All aqueous solutions were prepared with purified water (18 $M\Omega^{cm}$) using Milli-Q system (Millipore, USA). Sulfosuccinimidyl-4-(N-maleimidomethyl)cyclohexane-1-carboxylate (Sulfo-SMCC) and dithiothreitol (DDT) were purchased from Thermo Scientific Pierce (USA). Ethyl acetate and phosphate buffered saline (PBS, pH 7.4, 10 mM) were purchased from Sigma Aldrich (USA).

Genomic Engineering of *Pseudomonas aeruginosa* Azurin

Genomic DNA was isolated from *Pseudomonas aeruginosa* using DNA purification kit (QIAZEN, USA). The forward primer was designed to contain the NdeI restriction site and the reverse primer was designed to contain the BamHI restriction site as follows:

```
                                       (SEQ ID NO: 37)
   Azu W F: 5'-CATATGCTACGTAAACTCGCTGCCGTA-3'

(SEQ ID NO: 38)
   Azu W R: 5'-GAATTCACTTCAGGGTCAGGGTGCCCT-3'.
```

Figure 1:
FIG. 1 shows a schematic diagram of the design of a three-cysteine and C-terminal RGD-introduced azurin.
Figure 1:
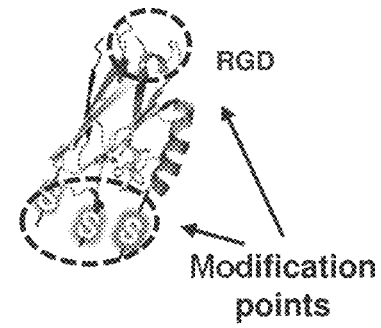
Figure 2:
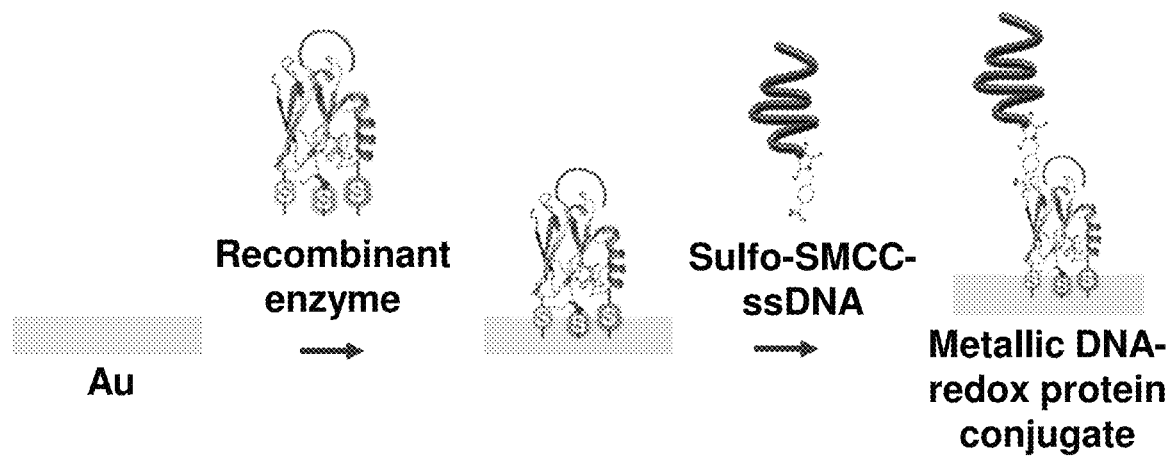
FIG. 2 shows a schematic diagram of the fabrication procedure of a biomoletron bottom portion (three-cysteine and C-terminal RGD-introduced azurin-ssDNA double layer).

A gene (SEQ ID NO: 7) coding blue copper protein azurin from the genomic DNA of *Pseudomonas aeruginosa* and the designed primers were amplified by using polymerase chain reaction (PCR). PCR reaction products were purified using the DNA purification kit (QIAZEN, USA), and then digested with two restriction enzymes NdeI and BamHI (New England Biolabs, UK). The digested DNA fragments were ligated to pET-21a(+) vector (Novagen, Germany), which have already been treated with NdeI and BamHI, using a ligation kit (Takara, Japan). The plasmids containing the obtained azurin gene, the Azu Cys1 F, Azu Cys2 F, Azu Cys3 F, Azu RGD F and Azu Cys1 R, Azu Cys2 R, Azu Cys3 R, Azu RGD R primers, which were designed to induce site-specific mutation, and QuikChange Lightning Multi Site-Directed Mutagenesis kit (Agilent Technologies, USA) were used to produce mutation, so that ATG was substituted with TGC, AAG was substituted with TGC, and CTG was substituted with TGC, that is, Met13Cys(M13C), Lys92Cys (K92C), and Leu39Cys(L39C), and that the RGD amino acids were inserted in the C-terminal. The azurin gene was mutated using site-specific mutation (FIG. 1). The mutated gene sequence was reconfirmed through sequencing.

For subcloning, *Escherichia coli* DH5a was used. Herein, for use of site-specific mutation of the azurin gene, the primers of azurin protein were designed as shown in Table 1.

TABLE 1

| Primer name | Forward sequence | Reverse sequence |
|---|---|---|
| Azu Cys1 | 5-CATCCAGGGTAACGACCAGTGCC AGTTCAACACCAATGCCA-3 (SEQ ID NO: 39) | 5-TGGCATTGGTGTTGAACTGGCACTG GTCGTTACCCTGGATG-3 (SEQ ID NO: 40) |
| Azu Cys2 | 5-GCTGATCGGCTCGGGCGAGTGCG ACTCGGTGACCTTCGACG-3 (SEQ ID NO: 41) | 5-CGTCGAAGGTCACCGAGTCGCACTC GCCCGAGCCGATCAGC-3 (SEQ ID NO: 42) |
| Azu Cys3 | 5-CCTGTCCCACCCCGGCAACTGCC CGAAGAACGTCATGGGCC-3 (SEQ ID NO: 43) | 5-GGCCCATGACGTTCTTCGGGCAGTT GCCGGGGTGGGACAGG-3 (SEQ ID NO: 44) |
| Azu RGD | 5-GCGCTGATGAAGGGCACCCTGAC CCTGAAGCGCGGGGATTGAGGAT CCGGCTGCTAACAAAGCCCGAAA-3 (SEQ ID NO: 45) | 5-TTTCGGGCTTTGTTAGCAGCCGGAT CCTCAATCCCCGCGCTTCAGGGTCA GGGTGCCCTTCATCAGCGC-3 (SEQ ID NO: 46) |

Expression and Purification of Recombinant Azurin Variants

The plasmids containing modified azurin gene were transformed into *E. coli* BL21 (DE3). The transformed strains were grown to an OD of 0.6 at 37° C. in shake flasks containing 1 L of LB medium (0.5% yeast extract, 1.0% tryptophan, and 1.0% NaCl) with 50 mg/ml ampicillin. The expression was induced by adding isopropyl beta-D-thiogalactopyranoside (IPTG) to a final concentration of 0.839 mM. The transformed cells were grown for an additional 16 hr at 37° C. The cells were harvested by centrifugation at 5000 g for 15 minutes at 4° C. The cell paste was suspended in sucrose buffer (20% sucrose, 0.3 M Tris-HCl, pH 8.1, and 1 mM EDTA) and subjected to osmotic shock (0.5 mM $MgCl_2$). Contaminating proteins were precipitated from the periplasmic preparation by decreasing the pH to 3.0, yielding azurin-containing supernatant. The three-cysteine and C-terminal RGD-introduced apo-azurin fractions (elution pH=5.2 and 5.4) were separated on a CM cellulose ion-exchange column with a pH gradient from 4.0 to 6.0 (50 mM sodium acetate). For the addition of copper ions into modified azurin proteins, 0.5 M CuSO4 was added. The three-cysteine and C-terminal RGD-introduced azurin proteins were separated by MWCO 5 k Amicon Ultra centrifugal filter (Millipore, USA).

Preparation and Purification of Sulfo-SMCC Tagged ssDNA

For the preparation of the three-cysteine and C-terminal RGD-introduced azurin-SMCC-DNA hybrid, the thiol group was modified at the 5'-end of the single strand DNA to be suitable for conjugation through sulfo-SMCC between recombinant azurin and ssDNA (single stranded DNA). ssDNA was provided from Bioneer (Korea), and was designed as follows:

(SEQ ID NO: 3)
ssDNA:
5'-CGCGCGCCGCTTTAGAGCGCGCGCGATTTCTGCATATATA-3'.

The thiol-modified ssDNA (sulfhydryl-containing biomolecule) was reacted with sulfo-SMCC.

More specifically, 1 ml of 5 µM thiol-modified ssDNA (40 mer) diluted with PBS buffer (pH 7.4) was prepared. For thiol-modified ssDNA activation, the thiol-modified ssDNA was additionally reduced by treatment with 100 µl of 1.0 N DTT at room temperature for 15 minutes, obtaining a free sulfhydryl group. Then, the saturated DTT was removed by adding 1 ml of ethyl acetate to the DNA solution. The reduced thiol-modified ssDNA was transferred to a hybridization buffer by using a desalting column (PD-10). During the preparation of free SH-DNA, 0.5 mg of sulfo-SMCC was added to 100 µl of tertiary distilled water, followed by reaction in a water bath at 50° C. for 10 minutes, thereby preparing 100 µl of 5 µM sulfo-SMCC. For conjugation of 1 ml of 5 µM free SH-DNA and 100 µ/L of 5 µM sulfo-SMCC, shaking was carried out in a refrigerator at 4° C. for 4 hours. Then, the sulfo-SMCC tagged ssDNA was purified, and unreacted materials were removed by ultrafiltration (MWCO 3 k Amicon Ultra centrifugal filter, Millipore, USA).

Preparation of Biomoletron Bottom Portion (Three-Cysteine and C-Terminal RGD-Introduced Azurin-ssDNA Double Layer) (Part 1)

Figure 3:
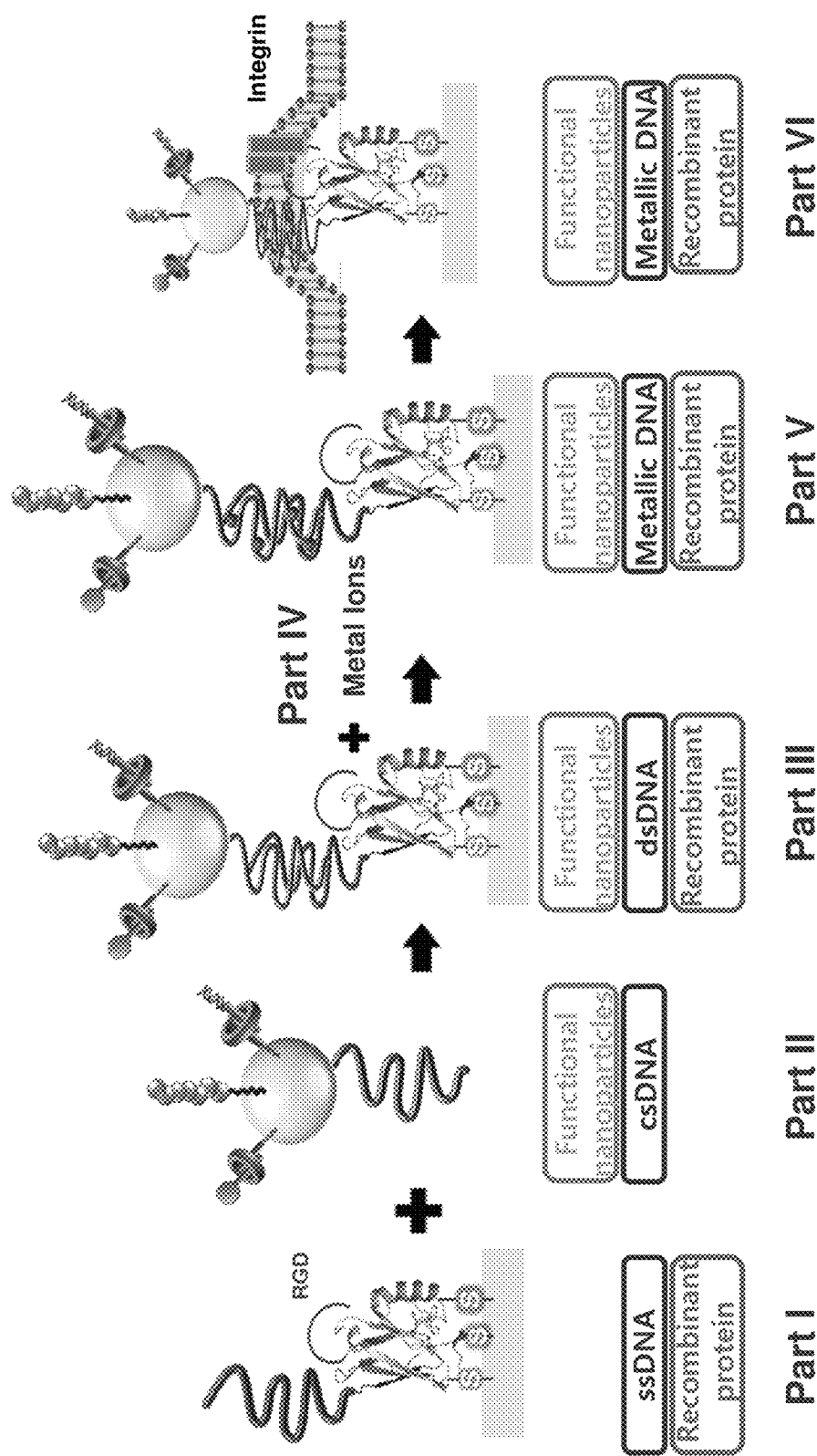
FIG. 3 shows a schematic diagram of the fabrication procedure of a biomoletron for controlling stem cell differentiation

Au substrates (Au (100 nm)/Cr (5 nm)/$SiO_2$/Si wafer) diced into 5 mm×15 mm were purchased from National NanoFab Center (Korea). For the preparation of a working electrode of a biomoletron, gold (Au) working electrodes were massively prepared on the Si/$SiO_2$ substrates. The prepared Au electrodes were washed with a piranha solution (30 vol % $H_2O_2$ and 70 vol % $H_2SO_4$) at 70° C. for 3 minutes. The gold electrodes were washed, repeatedly washed with ethanol and deionized water, and then dried under nitrogen streams. Then, 20 µl of the prepared 0.1 mg/ml solution of three-cysteine and C-terminal RGD-introduced azurin was allowed to stand on the Au surface for 4 hours for direct immobilization on the Au surface via the cysteine resides. After 4 hours, the resultant substrates were washed with tertiary distilled water and dried under nitrogen streams. The recombinant azurin-immobilized gold substrates were immersed in 20 µl of 5 µM solution of sulfo-SMCC tagged ssDNA for 2 hours. For the formation of the recombinant azurin/ssDNA double layer, a covalent bond between the amine group of the recombinant azurin and the sulfo group of the sulfo-SMCC tagged ssDNA was used. This procedure was carried out in a humidification chamber at 25° C. After 2 hours, the recombinant azurin/ssDNA double layer immobilized double layer was formed. For removal of unreacted sulfo-SMCC tagged ssDNA, the resultant substrates was washed with deionized water and dried under nitrogen gas (FIG. 3).

Preparation and Purification of Biomoletron Top Portion (Bio-Functional Nanoparticle-csDNA Conjugate) (Part II)

Au substrates (Au (10 nm)/Cr (12 nm)/SiO$_2$/Si wafer) diced into 12 mm×35 mm were purchased from G-mek (Korea). For the preparation of the bio-functional nanoparticle-csDNA conjugate, 5'-end thiol-modified ssDNA 2 (single strand DNA 2) for conjugation to a metal plate and 5'-end thiol-modified csDNA 2 (complementary strand DNA 2) for conjugation to 5-nm gold nanoparticle were purchased from Bioneer (Korea), and primer sequences were designed as follows:

```
                                       (SEQ ID NO: 47)
ssDNA 2: 5'-ATAAAAAAAACGCGGGGGTTCCGCG-3'

(SEQ ID NO: 48)
csDNA 2: 5'-GCGCCCCCAAGGCGCAAAAATAAAA-3'
```

The 5-nm gold nanoparticles were purchased from BBI International (UK), 5,5'-Bis(mercaptomethyl)-2,2-bipyridine, Cucibit [8] Uril (CB), N-hydroxysuccinimide (NHS), 1-ethyl-3-(–3-dimethylaminopropyl)carbodiimide hydrochloride (EDC), and phosphate buffered saline (PBS, pH 7.4, 10 mM) were purchased from Sigma Aldrich (USA). A cell-penetrating peptide (CPP) for penetrating cell membranes, and peptides (peptide 1 (C-t NH$_2$ group), peptide 2 (C-t Cys)) for preparing a bio-functional nanoparticle hybrid were synthesized, and designed as follows:

```
CPP (CTAT):        CGRKKRRQRRRPQ (SEQ ID NO: 49)

Peptide 1 (C-t NH₂): TGG-NH₂ (SEQ ID NO: 50)

Peptide 2 (C-t Cys): WGGC. (SEQ ID NO: 51)
```

The retinoic acid (RA) as a neural stem cell differentiation inducer was synthesized by Sigma Aldrich (USA), and siSOX9, one type of siRNA, was synthesized from the modification of a maleimide group at the 5'-end by Bioneer (Korea). siSOX9 was designed as follows:

```
                                      (SEQ ID NO: 5)
siSOX9 antisense:
5'-Maleimide-AACGAGAGCGAGAAGAGACCC-3'

(SEQ ID NO: 6)
siSOX9 sense:
5'-Maleimide-GGGUCUCUUCUCGCUCUCGUU-3'.
```

The csDNA (complementary strand DNA), which is complementary to the biomoletron bottom portion (three-cysteine and C-terminal RGD-introduced Azurin-ssDNA double layer) was purchased from Bioneer (Korea), and was designed as follows:

```
                                      (SEQ ID NO: 4)
csDNA:
5'-TATATATGCAGAAATCCCCCCCCCTCTAAAGCGGCGCGCG-3'.
```

For fabricating the biomoletron top portion (bio-functional nanoparticle-csDNA conjugate), mungbean nuclease was purchased from New England Biolabs (USA).

For the preparation of the biomoletron top portion (bio-functional nanoparticle-csDNA conjugate), peptide 1, RA, and EDC/NHS in eppendorf tube 1 and peptide 2, 5'-end maleimide-modified siSOX9 antisense, and siSOX9 sense in eppendorf tube 2 were reacted for 4 hours in a shaking incubator in a refrigerator at 4° C. The Au substrates diced into 12 mm×35 mm were washed with a base piranha solution (15 vol % H$_2$O$_2$, 15 vol % NH$_4$OH, and 70 vol % H$_2$O) at 70° C. for 3 minutes. Au electrodes were washed, repeatedly washed with ethanol and deionized water, dried under nitrogen streams, and then put on a 60×15 mm Petri dish. For the direct immobilization on the metal substrate, 3 ml of 10 mM PBS (pH 7.4) and 100 μl of 5 μM 5'-end thiol-modified ssDNA 2 were mixed, followed by standing for 2 hours. After 2 hours, the substrate was washed with tertiary distilled water, dried under nitrogen streams, and put on a 60×15 mm Petri dish. For complementary conjugation thereto, 3 ml of 10 mM PBS (pH 7.4) and 100 μl of 5 μM csDNA 2 were mixed, followed by immersion for 1 hour. After 1 hour, the resultant substrates were washed with tertiary distilled water, dried under nitrogen streams, and put on a 60×15 mm Petri dish. For the conjugation of the thiol-modified csDNA 2 and the 5-nm gold nanoparticle to the gold substrate, 3 ml of 10 mM PBS (pH 7.4) and 5 nm-sized gold nanoparticles were immobilized for 2 hours. After 2 hours, the resultant substrates were washed with tertiary distilled water, dried under nitrogen streams, and put on a 60×15 mm Petri dish. For making bio-functional nanoparticle-dsDNA hybrid 1, 3 ml of 10 mM PBS (pH 7.4) and 5,5'-bis(mercaptomethyl)-2,2-bipyridine and CPP (CTAT) at a molar ratio of 2:1 were mixed on the gold nanoparticle-dsDNA hybrid, followed by standing for 2 hours. After 2 hours, the resultant substrates were washed with tertiary distilled water, dried under nitrogen streams, and put on a 60×15 mm Petri dish. For the preparation of bio-functional nanoparticle-dsDNA hybrid 2, eppendorf tube 1, eppendorf tube 2, and Cucibit [8] Uril (CB), which have been reacted with 3 ml of 10 mM PBS (pH 7.4), were mixed at a molar ratio of 1:1:2, followed by standing for 2 hours. After 2 hours, the resultant substrates were washed with tertiary distilled water, dried under nitrogen streams, and put on a 60×15 mm Petri dish. For making bio-functional nanoparticle-dsDNA hybrid 3, 3 ml of 10 mM PBS (pH 7.4) and 10 units of mungbean nuclease dissolved in mungbean nuclease reaction buffer were conducted for 1 hour in an incubator at 37° C. After 1 hour, the solution in the Petri dish was collected in the eppendorf tubes. For the purification of only bio-functional nanoparticle-dsDNA hybrid 3 in the collected solution, 0.2 μm-syringe filter was, first, used to remove the agglomerated bio-functional nanoparticle-dsDNA hybrid 3. Unreacted materials were, second, removed through ultrafiltration (MWCO 50 k Amicon Ultra centrifugal filter, Millipore, USA). The bio-functional nanoparticle-dsDNA hybrid 3 separated after ultrafiltration was reacted with the biomoletron bottom portion (three-cysteine and C-terminal RGD-introduced azurin-ssDNA double layer) and 20 μl of 5 μM complementary thiol-modified csDNA. For the purification of bio-functional nanoparticle-csDNA conjugate, unreacted materials were removed through ultrafiltration (MWCO 50 k Amicon Ultra centrifugal filter, Millipore, USA) (FIG. 3).

Fabrication of Biomoletron (Parts III, IV, and V)

For the fabrication of the biomoletron (Part III), 20 μl of the biomoletron top portion (bio-functional nanoparticle-csDNA conjugate) was allowed to stand for 1 hour by using the fact that ssDNA of the substrate with the biomoletron bottom portion (three-cysteine and C-terminal RGD-introduced azurin-ssDNA double layer) is complementary to csDNA of the biomoletron top portion (bio-functional nanoparticle-csDNA conjugate). After 1 hour, the resultant substrate was washed with tertiary distilled water and dried under nitrogen streams. For the fabrication of the biomoletron (Part V), the resultant substrate was immersed in 10

μl of 10 mM $AgNO_3$ solution for 1 hour. The introduction of metal ions into DNA nucleotide pairs of the biomoletron increases the electron delivery efficiency from the gold substrate to the bio-functional nanoparticle.

After 1 hour, the resultant substrate was washed with tertiary distilled water and dried under nitrogen streams (FIG. 3).

Detection of Hydrogen Peroxide by Amperometric Measurement

For use as a working electrode, 20 μl of 0.1 mg/ml solution of three-cysteine and C-terminal RGD-introduced azurin was directly immobilized to the Au substrate (Au(100 nm)/Cr(5 nm)/$SiO_2$/Si wafer) of 5 mm×15 mm treated with a base piranha solution. The amperometric measurement was performed using the fabricated working electrode according to various concentrations of hydrogen peroxide. The amperometric measurement was performed by a 3-electrode system using Au/azurin substrate as a working electrode, platinum as a counter electrode, and Ag/AgCl/$KCl_{sat}$ as a reference electrode. To 5 ml of 10 mM PBS (pH 7.4), 20 μl of 100 μM hydrogen peroxide was consecutively added, and the current-time curve was recorded while the potential was set to 0V. During the measurement of current, the convection was moved with magnetic stirring at 600 rpm. The buffer solution added in the experiments was removed by high-purity nitrogen. The CHI 660A potentiostat equipped with general purpose electrochemical software was used in the experiments.

Figure 4:
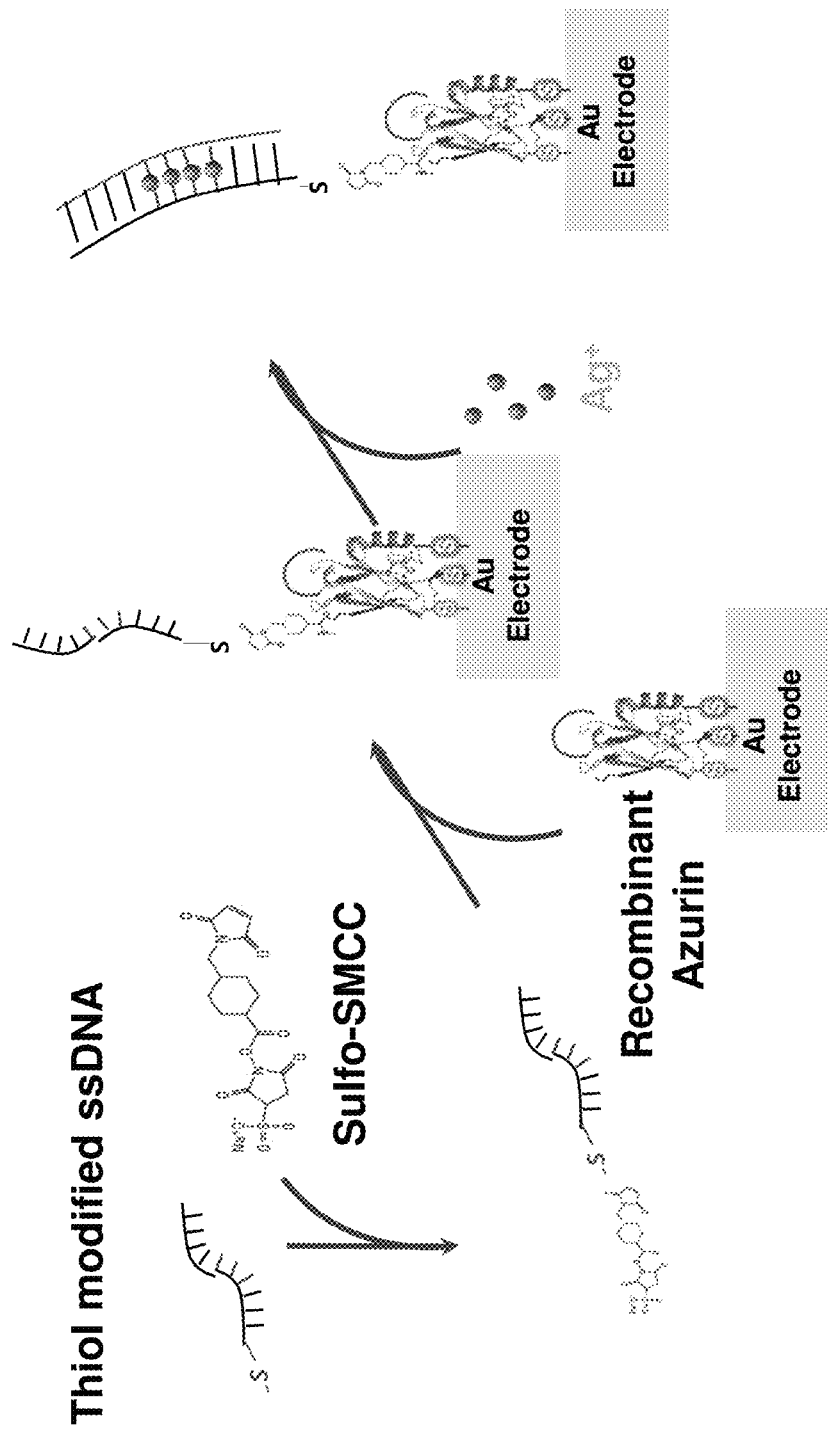
FIG. 4 shows a schematic diagram of the fabrication procedure of an Au/azurin/metal ion meditated-nucleotide pair for conductivity confirmation.
Figure 5:
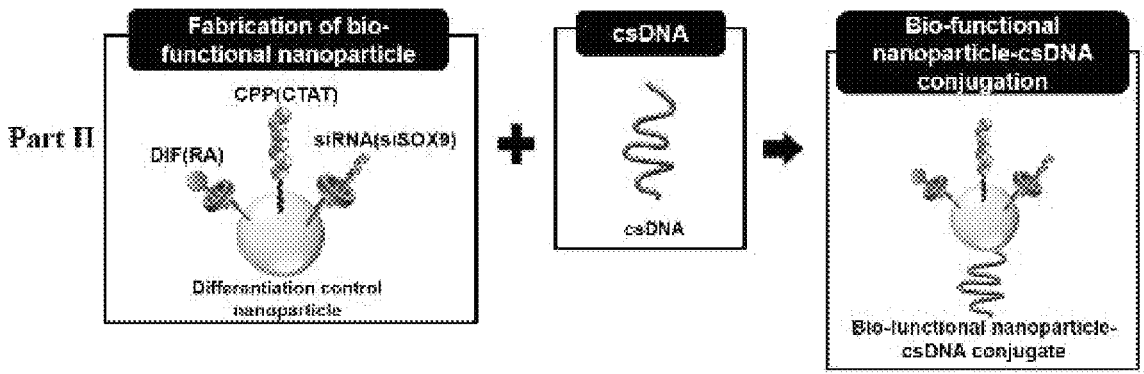
FIG. 5 shows a schematic diagram of the fabrication procedure of a biomoletron top portion (bio-functional nanoparticle-csDNA conjugate).
Figure 5:
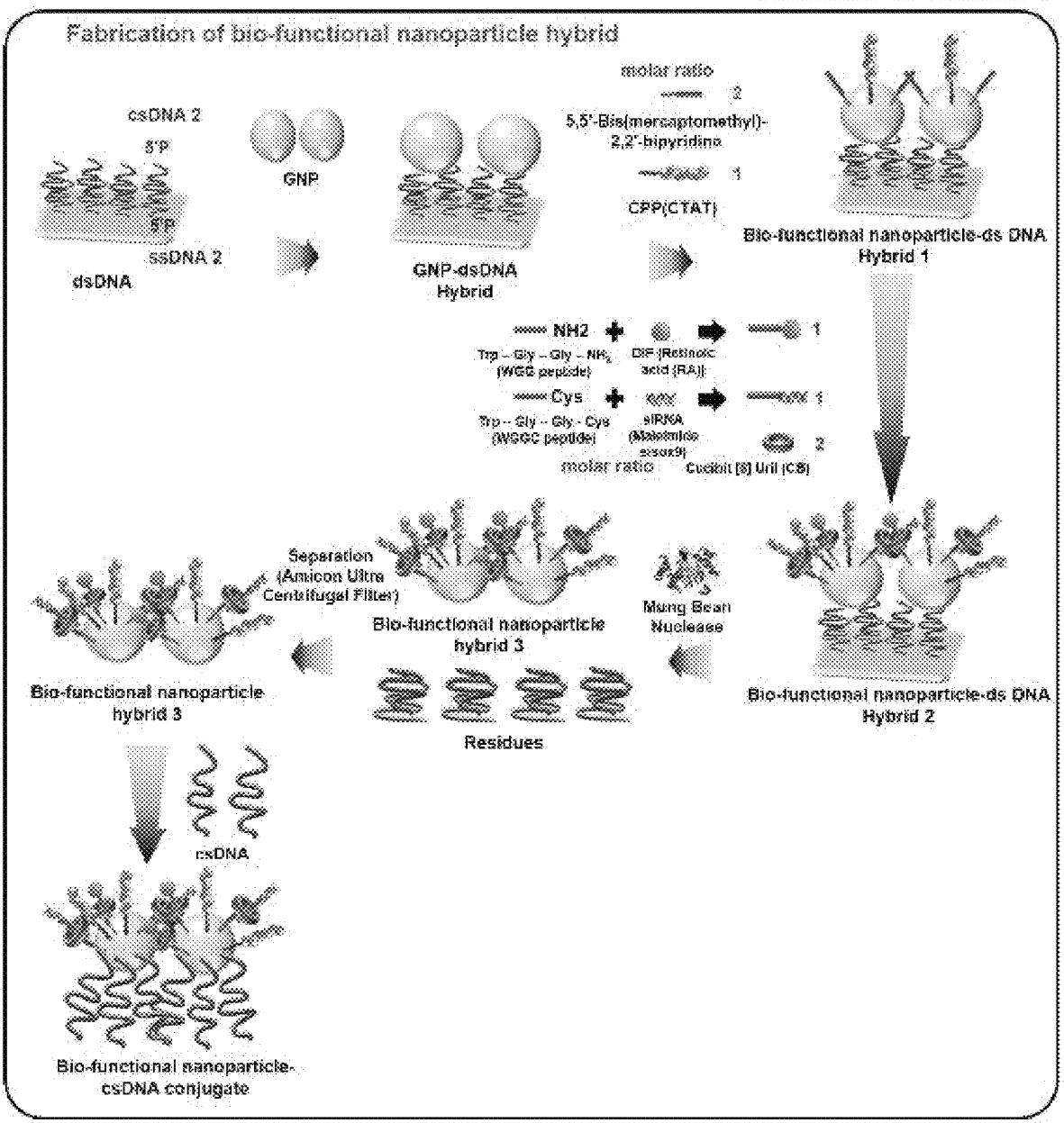

Cyclic Voltammetry Experiments for Investigating Conductivity of Au/Azurin/Metal Ion-Mediated Nucleotide Pair 20 μl of the prepared 7 μM solution of three-cysteine and C-terminal RGD-introduced azurin was allowed to stand on a gold surface of the 5 mm×15 mm Au substrate (Au (100 nm)/Cr (5 nm)/SiO2/Si wafer) treated with the piranha solution for 4 hours for direct immobilization on the gold surface via the cysteine resides. After 4 hours, the resultant substrate was washed with tertiary distilled water and dried under nitrogen streams. Thereafter, the recombinant azurin-immobilized gold substrate was immersed in 20 μl of 5 μM solution of sulfo-SMCC tagged ssDNA for 2 hours. After 2 hours, the resultant substrate was washed with tertiary distilled water and dried under nitrogen streams. Thereafter, 20 μl of csDNA complementary to ssDNA of Au/azurin/ssDNA was allowed to stand for 1 hour. After 1 hour, the resultant substrate was washed with tertiary distilled water and dried under nitrogen streams. For the fabrication of Au/azurin/metal ion-mediated nucleotide pair, the resultant substrate was immersed in 10 μl of 10 mM $AgNO_3$ solution for 1 hour. After 1 hour, the resultant substrate was washed with tertiary distilled water and dried under nitrogen streams. The fabricated chip was used as a working electrode. The present system is a conventional 3-electrode system composed of a working electrode, a counter electrode, and a reference electrode. Pt counter electrode and Ag/AgCl reference electrode were purchased from BSA (USA). Electrochemical experiments were conducted by CHI660A electrochemical workstation. All the electrochemical experiments were conducted in 10 mM PBS (pH 7.4) (FIG. 4).

Electrochemical Experiments and Fluorescence Microscope for Confirmation of Electric Release Functions For electrochemical experiments and fluorescence microscopic assay, peptides (peptide 3, peptide 4(C-t FITC)) were synthesized, and designed as follows.

Peptide 3: WGG

Peptide 4(C-t FITC): WGG-FITC

A chemical material complex with a thiol group was immobilized for 3 hours on the 5 mm×15 mm Au substrate (Au (100 nm)/Cr (5 nm)/SiO2/Si wafer) treated with the piranha solution. The chemical substance complex was composed of 5,5'-bis(mercaptomethyl)-2,2'-bipyridine, Cucibit [8] Uril (CB), and peptide 3, and prepared by a self-assembly method. After 3 hour, the resultant substrate was washed with tertiary distilled water and dried under nitrogen streams. The fabricated chip was used as a working electrode. Amperometric measurement and cyclic voltammetry were carried out using the fabricated working electrode. The present system is a conventional 3-electrode system composed of a working electrode, a counter electrode, and a standard electrode. Pt counter electrode and Ag/AgCl reference electrode were purchased from BSA (USA). Electrochemical experiments were conducted by CHI660A electrochemical workstation (CH Instrument, USA). All the electrochemical experiments were conducted in 10 mM PBS (pH 7.4) buffer solution. For fluorescence microscopic analysis, a chemical substance complex with a thiol group was immobilized for 3 hours on the 5 mm×15 mm Au substrate (Au (100 nm)/Cr (5 nm)/SiO2/Si wafer) treated with the piranha solution. The chemical substance complex was composed of 5,5'-bis(mercaptomethyl)-2,2'-bipyridine, Cucibit [8] Uril (CB), and peptide 4, and made by a self-assembly method. After 3 hours, the resultant substrate was washed with tertiary distilled water under nitrogen streams. The fabricated sample was examined by a fluorescence microscope (Nikon Eclipse Ti-U, USA).

Biomoletron Surface Investigation Using Flow Surface Plasmon Resonance (Flow SPR).

For the investigation of biofilms, a surface plasmon resonance instrument (Reichert SR7500DC Dual Channel System, USA) was used, and Scrubber2 (Reichert, USA) was used as data analysis software. The 12.5 mm×12.5 mm-sized gold substrate (Au (50 nm)/Cr (1 nm)/glass slide (0.95 mm)) was purchased from Reichert (USA), and treated with oil to reduce air and bubbles between gold and prism. Detailed experimental conditions of flow surface plasmon resonance are shown in Table 2 below.

TABLE 2

| Order | Sample | Concentration | Flow rate | Association time (sample injection) | Dissociation time (buffer loading) |
|---|---|---|---|---|---|
| 1. Ligand | Recombinant Azurin with RGD | 10 ug | 20 ul/min | 6 min | 4 min 30 sec |
| 2. Ligand | Recombinant Azurin with RGD | 15 ug | 20 ul/min | 6 min | 25 min |
| 3. Analyte 1 | ssDNA | 5 uM | 30 ul/min | 5 min | 5 min |
| 4. Analyte 2 | scDNA-Functional GNP complex | 5 uM | 30 ul/min | 4 min | 3 min |

TABLE 2-continued

| Order | Sample | Concentration | Flow rate | Association time (sample injection) | Dissociation time (buffer loading) |
|---|---|---|---|---|---|
| 5. Analyte 2 | scDNA-Functional GNP complex | 5 uM | 30 ul/min | 4 min 20 sec | 4 min 30 sec |
| 6. Analyte 3 | Metal Ion (Ag$^+$) | 5 uM | 30 ul/min | 5 min | 5 min |

Confirmation of Biomoletron Release System Using Amperometric Measurement and Surface Plasmon Resonance (SPR)

40 µl of the prepared 7 µM solution of three-cysteine and C-terminal RGD-introduced azine was allowed to stand on a gold surface of the 12.5 mm×12.5 mm Au substrate (Au (50 nm)/Cr (1 nm)/glass slide (0.95 mm) treated with the piranha solution for 4 hours for direct immobilization on the surface of the gold substrate via the cysteine resides. After 4 hours, the resultant substrate was washed with tertiary distilled water and dried under nitrogen streams. Thereafter, the recombinant azurin-immobilized gold substrate was immersed in 40 µl of 5 µM solution of sulfo-SMCC tagged ssDNA for 2 hours. After 2 hours, the resultant substrate was washed with tertiary distilled water and dried under nitrogen streams. For the fabrication of the biomoletron (Part III), 40 µl of the biomoletron top portion (bio-functional nanoparticle-csDNA conjugate) was allowed to stand for 1 hour by using the fact that ssDNA of the substrate with the biomoletron bottom portion (three-cysteine and C-terminal RGD-introduced azurin-ssDNA double layer) is complementary to csDNA of the biomoletron top portion (bio-functional nanoparticle-csDNA conjugate). After 1 hour, the resultant substrate was washed with tertiary distilled water and dried under nitrogen streams. For the fabrication of the biomoletron (Part V), the resultant substrate was immersed in 20 µl of 10 mM AgNO$_3$ solution for 1 hour. After 1 hour, the resultant substrate was washed with tertiary distilled water and dried under nitrogen stream. The fabricated chip was used as a working electrode. The amperometric measurement was performed using the fabricated working electrode. All electrochemical experiments were conducted in 10 mM PBS (pH 7.4) buffer solution.

For confirmation of the biomoletron release system, a surface plasmon resonance instrument (Reichert SR7500DC Dual Channel System, USA) was used, and Scrubber2 (Reichert, USA) was used as data analysis software. The 12.5 mm×12.5 mm-sized gold substrate (Au (50 nm)/Cr (1 nm)/glass slide (0.95 mm)) was purchased from Reichert (USA), and treated with oil to reduce air and bubbles between gold and prism.

Fabrication of Biomoletron-Immobilized Working Electrode for Neural Stem Cells

In the present invention, a general 3-elecrochemical system composed of a working electrode (Au), a counter electrode (Pt), and a reference electrode (Ag/AgCl) was introduced. Au substrates (Au (10 nm)/Cr (2 nm)/glass wafer) diced into 12 mm×35 mm were purchased from G-mek (Korea). This substrate was semi-transparent, whereby the cells on the electrode could be easily observed through an optical microscope. The electrode was washed by sonication in alcohol and distilled water for 5 min. Au substrates diced into 12 mm×35 mm were washed with a base piranha solution (15 vol % H$_2$O$_2$, 15 vol % NH$_4$OH, and 70 vol % H$_2$O) at 70° C. for 3 minutes. Au electrodes were washed, repeatedly washed with ethanol and deionized water, dried under nitrogen streams, and then put on a 90×15 mm Petri dish. For electrochemical measurement, a plastic chamber (Lab-Tek®, Thermo fisher scientific, USA) was fixed to the gold working electrode using polydimethylsiloxane (PDMS), thereby fabricating a 10 mm×20 mm×5 mm (width×length×height) cell chip chamber with a 10 mm×20 mm exposure region. 120 µl of the prepared 7 µM solution of three-cysteine and C-terminal RGD-introduced azine was allowed to stand on a gold surface of the fabricated cell chip chamer Au substrate for 4 hours for direct immobilization on the gold surface via the cysteine resides. After 4 hours, the resultant substrate was washed twice with 10 mM PBS(pH 7.4) buffer, followed by suction with Pasteur pipette. Thereafter, the recombinant azurin-immobilized cell chip chamber Au substrate was immersed in 120 µl of 5 µM solution of sulfo-SMCC tagged ssDNA for 2 hours. After 2 hours, the resultant substrate was twice washed with 10 mM PBS (pH 7.4) buffer, followed by suction with Pasteur pipette. 120 µl of the biomoletron top portion (bio-functional nanoparticle-csDNA conjugate) was allowed to stand for 1 hour by using the fact that ssDNA of the cell chip chamber Au substrate with the biomoletron bottom portion (three-cysteine and C-terminal RGD-introduced azurin-ssDNA double layer) is complementary to csDNA of the biomoletron top portion (bio-functional nanoparticle-csDNA conjugate). After 1 hour, the resultant substrate was twice washed with 10 mM PBS (pH 7.4) buffer, followed by suction with Pasteur pipette. For the fabrication of the biomoletron on the fabricated cell chip chamber Au substrate, the resultant substrate was immersed in 60 µl of 10 mM AgNO$_3$ solution for 1 hour. After 1 hour, the resultant substrate was twice washed with 10 mM PBS (pH 7.4) buffer, followed by suction with Pasteur pipette.

Culture and Differentiation of Neural Stem Cells in Biomoletron-Immobilized Working Electrode The biomoletron-immobilized cell chip chamber Au substrate was used as a working electrode. NE4C cells were purchased from ATCC (Rockville, USA). For cell culture, MEM alpha medium (Gibco, USA) containing 10% heat-inactivated fetal bovine serum (FBS, Gibco, USA) and 1% penicillin (Gibco, USA) was used. The cells were incubated at 37° C. in humidified 5% CO$_2$ conditions. For differentiation of neural stem cells, a potential of −0.5 V was applied to the fabricated working electrode for 200 seconds using amperometric measurement. The medium was maintained for 3 days. Thereafter, the medium was replaced every two days. The cells were stained with tryptophan blue, and counted by haemocytomer.

Confirmation of Biomoletron-Based Stem Cell Differentiation Through Immunostaining The cells were fixed with 4% paraformaldehyde, and then permeated with 0.1% Triton X-100. After blocking with TBS-T containing 3% bovine serum albumin (BSA), the cells were incubated using indicated primary antibodies. The cells were washed, and then incubated using either Cy2— (Jackson ImmunoResearch Laboratories) or Alexa 594— (Life Technologies) conjugated secondary antibodies. The nuclei were stained with DAPI. Images were analyzed using a fluorescence microscope (Nikon Eclipse Ti-U, USA), and the primary antibodies used were Nestin, βIII-tubulin (Abcam, USA).

Confirmation of Biomoletron-Based Neural Stem Cell Differentiation Through RNA Extraction and Quantitative Reverse Transcription Polymerase Chain Reaction (RT-qPCR)

RNA was obtained using RNA extraction kit (QIAGEN, USA), and then was synthesized into complementary DNA (cDNA) according to a method provided using the First Strand cDNA synthesis kit (Thermo Scientific, USA).

RT-gPCR was conducted in Takara PCR thermal cycler (Takara, Japan), and gene-specific primers used in the present invention are clearly shown in table 3.

TABLE 3

| Gene | Forward sequence | Reverse sequence |
|---|---|---|
| Oct 4 | 5-GAGGCTACAGGGACACCTTTC-3 (SEQ ID NO: 52) | 5-GTGCCAAAGTGGGGACCT-3 (SEQ ID NO: 53) |
| NANOG | 5-AAATTGGTGATGAAGATGTATTCG-3 (SEQ ID NO: 54) | 5-GCAAAACAGAGCCAAAAACG-3 (SEQ ID NO: 55) |
| SOX2 | 5-TTCACATGTCCCAGCACTACCAGA-3 (SEQ ID NO: 56) | 5-TCACATGTGTGAGAGGGGCAGTGTGC-3 (SEQ ID NO: 57) |
| PAX6 | 5-TGTCCAACGGATGTGTGAGT-3 (SEQ ID NO: 58) | 5-TTTCCCAAGCAAAGATGGAC-3 (SEQ ID NO: 59) |
| Ngn2 | 5-ACATCTGGAGCCGCGTAG-3 (SEQ ID NO: 60) | 5-CAGCAGCATCAGTACCTCCTCt-3 (SEQ ID NO: 61) |
| Math2 | 5-CGACACTCAGCCTGAAAAGAt-3 (SEQ ID NO: 62) | 5-CAAACTTTCTGCACATCTGGG-3 (SEQ ID NO: 62) |
| ACTB | 5-GTCCTCTCCCAAGTCCACAC-3 (SEQ ID NO: 64) | 5-GGGAGACCAAAAGCCTTCAT-3 (SEQ ID NO: 65) |

Results

Figure 6A:
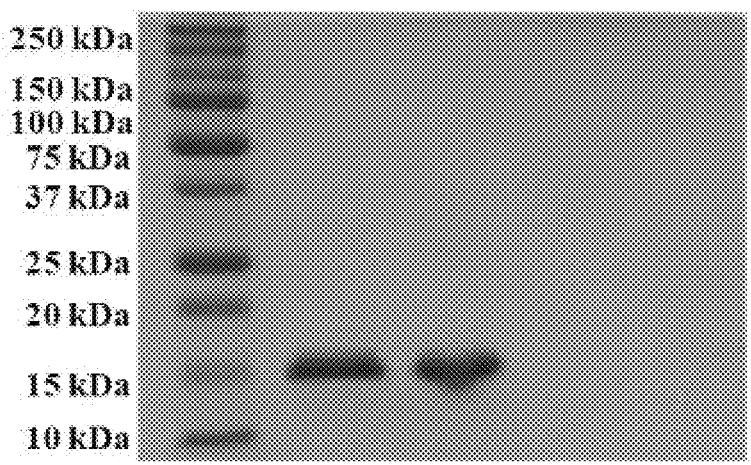
FIG. 6A shows the results of confirming the expression of recombinant azurin using electrophoresis.
Figure 6B:
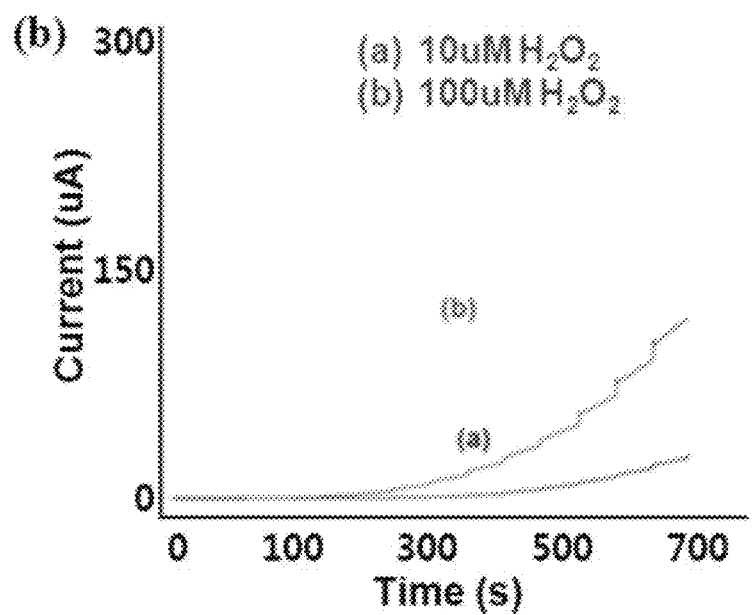
FIG. 6B shows the results of confirming the hydrogen peroxide scavenging potential of the recombinant azurin.

Confirmation of Expression and RGD Peptide Sequence-Introduced Recombinant Azurin and $H_2O_2$ Consumption Function Thereof FIG. 6 shows electrophoresis and hydrogen peroxide scavenging function of recombinant azurin. For direct immobilization with the integrin located on cell surfaces, the RGD peptide-modified gene was inserted to produce recombinant azurin, which was then confirmed by electrophoresis. The recombinant RGD peptide-introduced azurin was examined for a function of scavenging hydrogen peroxide, which is one of reactive oxygen species, using amperometric measurement.

Confirmation of Conductivity of Au/Azurin/Metal Ion Mediated-Nucleotide Pair

Figure 7A:
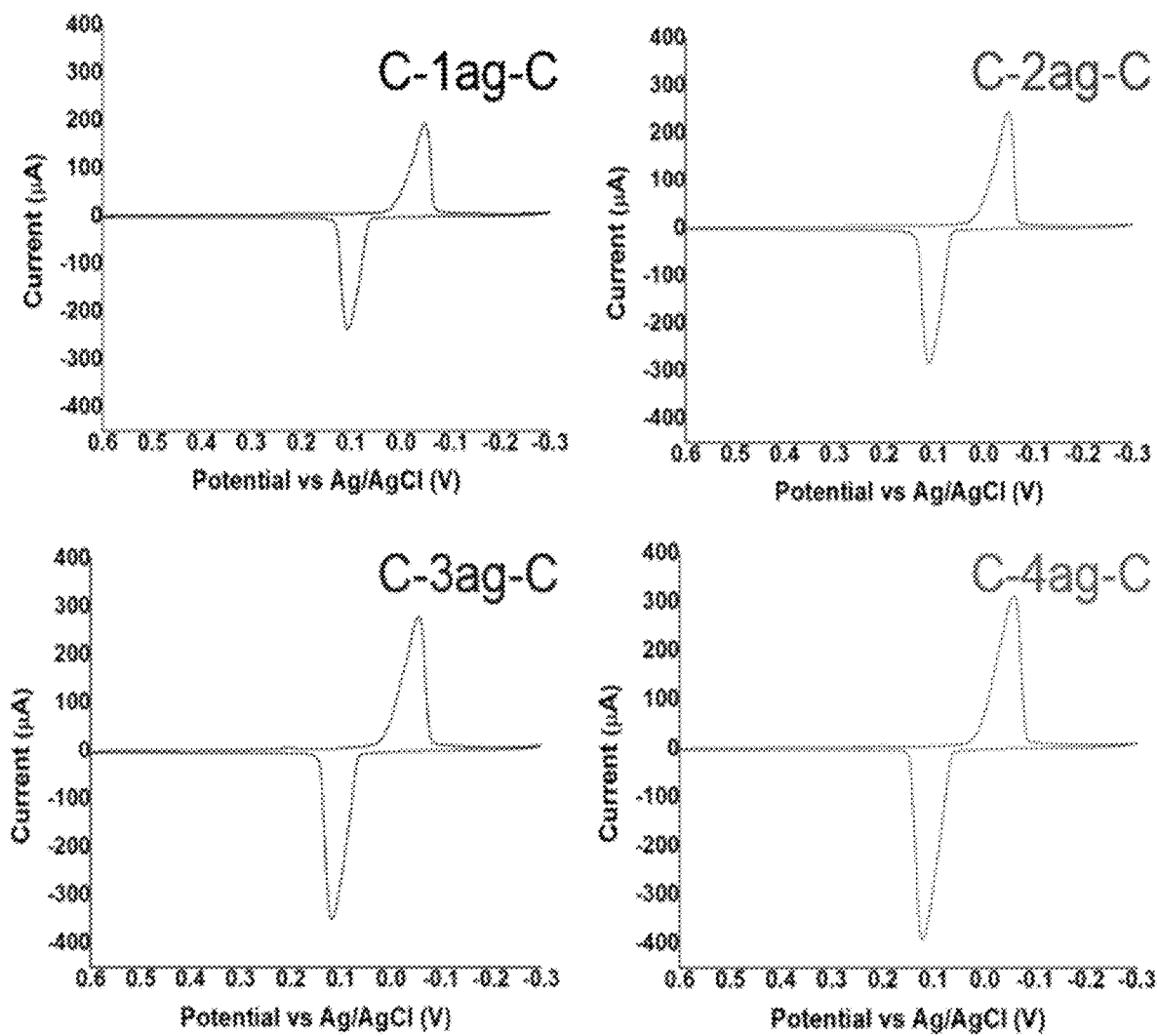
FIG. 7A shows the result of confirming the conductivity of Au/azurin/metal ion meditated-nucleotide pair using cyclic voltammetry.
Figure 7B:
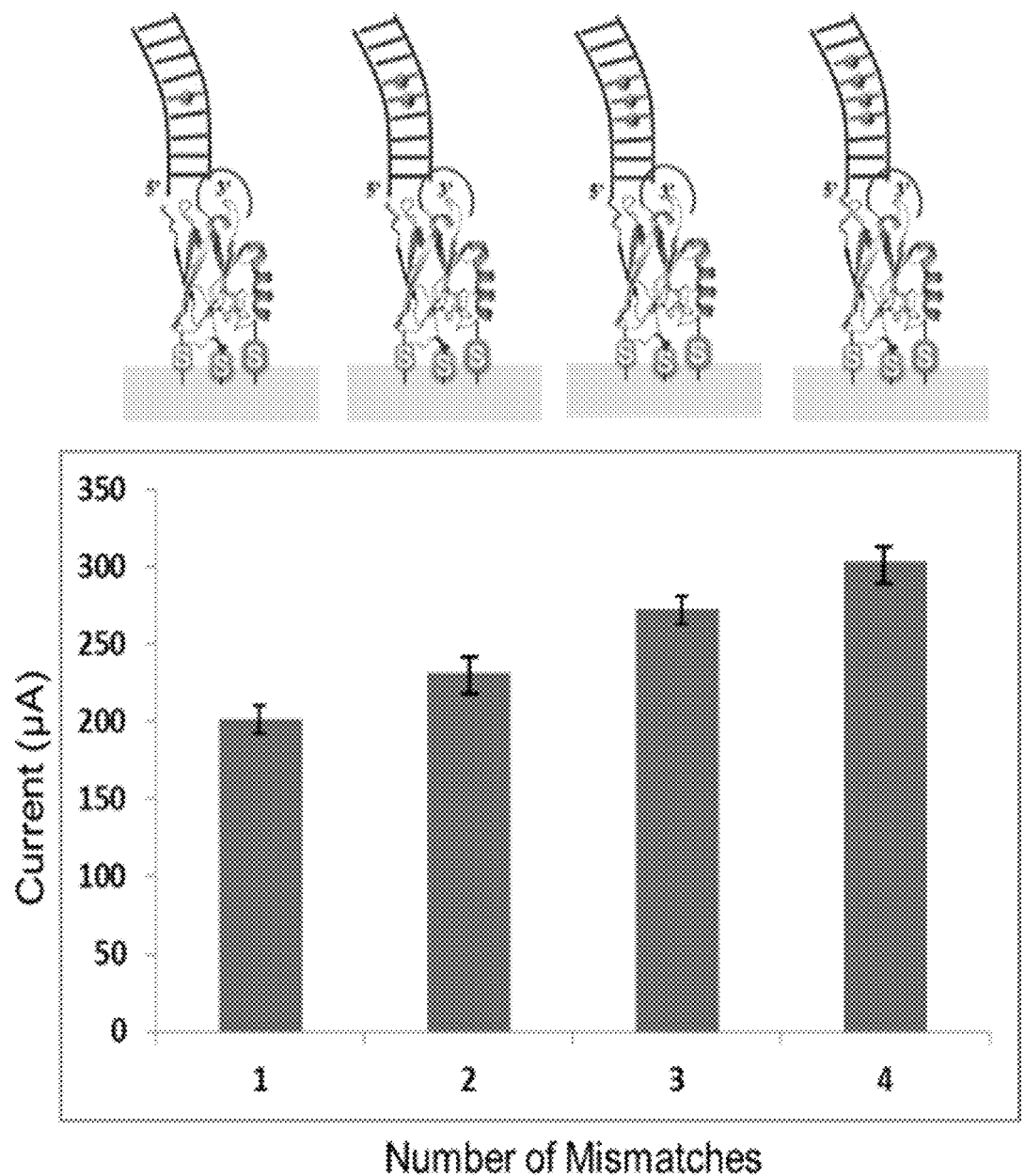
FIG. 7b shows an increase in conductivity according to the number of metal ions of the Au/azurin/metal ion meditated-nucleotide pair.

FIG. 7 shows an increase in conductivity according to the number of metal ions inserted. The metal-DNA was fabricated using a combination with specific metal ions, which can be inserted into sequence portions in which mismatches between DNA double strands are generated in the complementary binding of ssDNA and csDNA located on the cell surface, and an increase in conductivity according to the increase in the number of inserted metal ions was confirmed using the electrochemical method.

Confirmation of Electric Release Functions

Figure 8A:
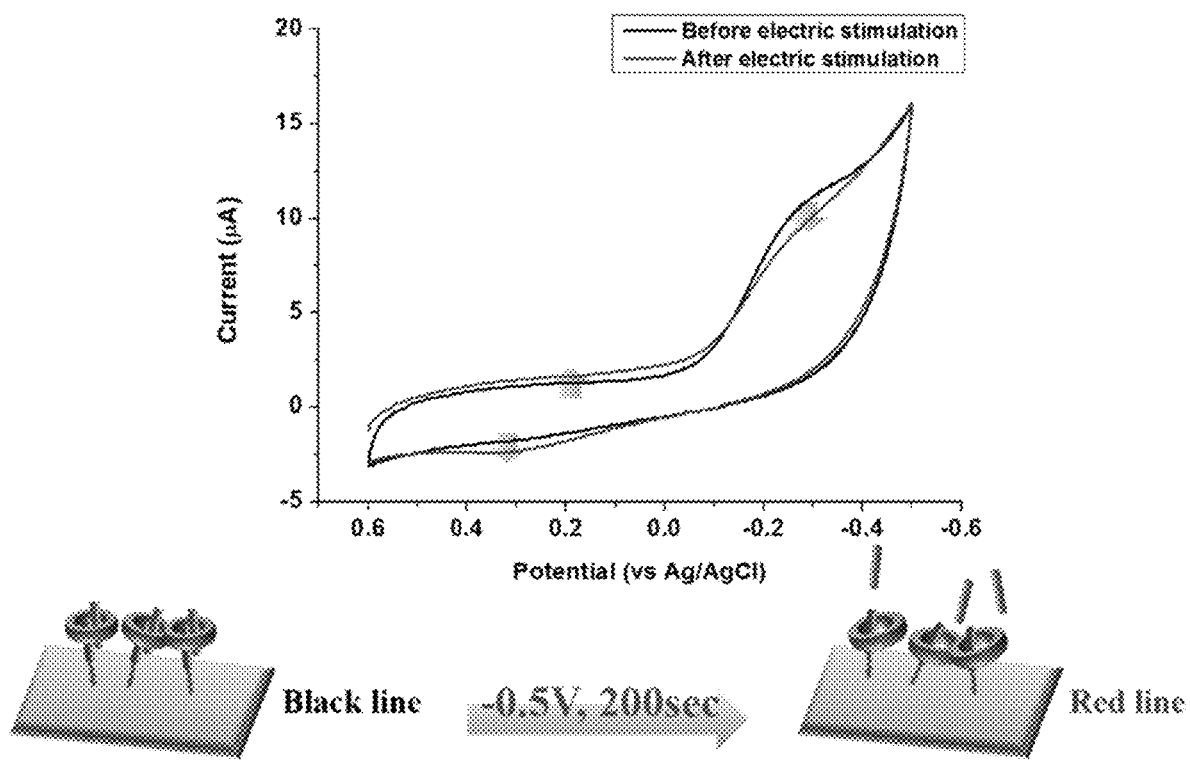
FIG. 8A shows electric release functions using cyclic voltammetry and fluorescence microscopy.
Figure 8B:
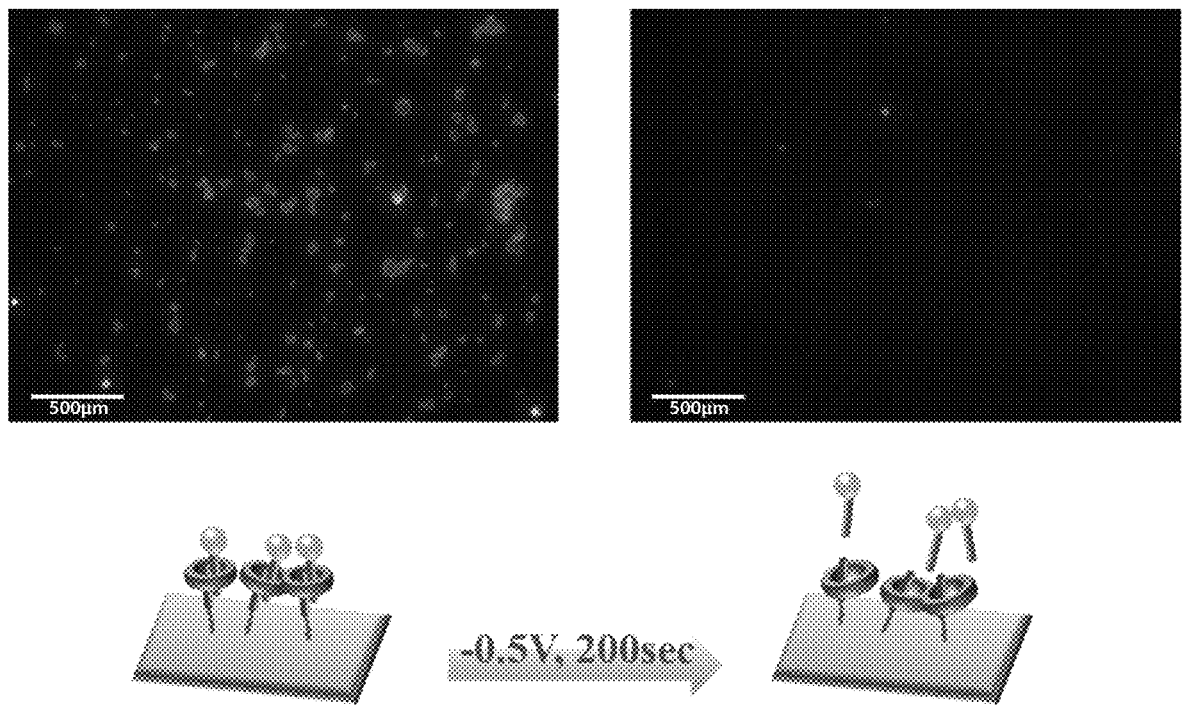
FIG. 8B shows electric release functions using cyclic voltammetry and fluorescence microscopy.

FIG. 8 shows the confirmation of the electric release functions using cyclic voltammetry and fluorescence microscopy. As a result of examining the curves before and after a potential of −0.5 V was applied to the working electrode for 200 seconds using amperometric measurement, a change in curve was confirmed, indicating the release of peptide 3. The release of peptide 4 was confirmed through a fluorescence microscope, indicating an electric release function.

Confirmation of Biomoletron Surface Verification Using Flow Surface Plasmon Resonance (Flow SPR).

Figure 9:
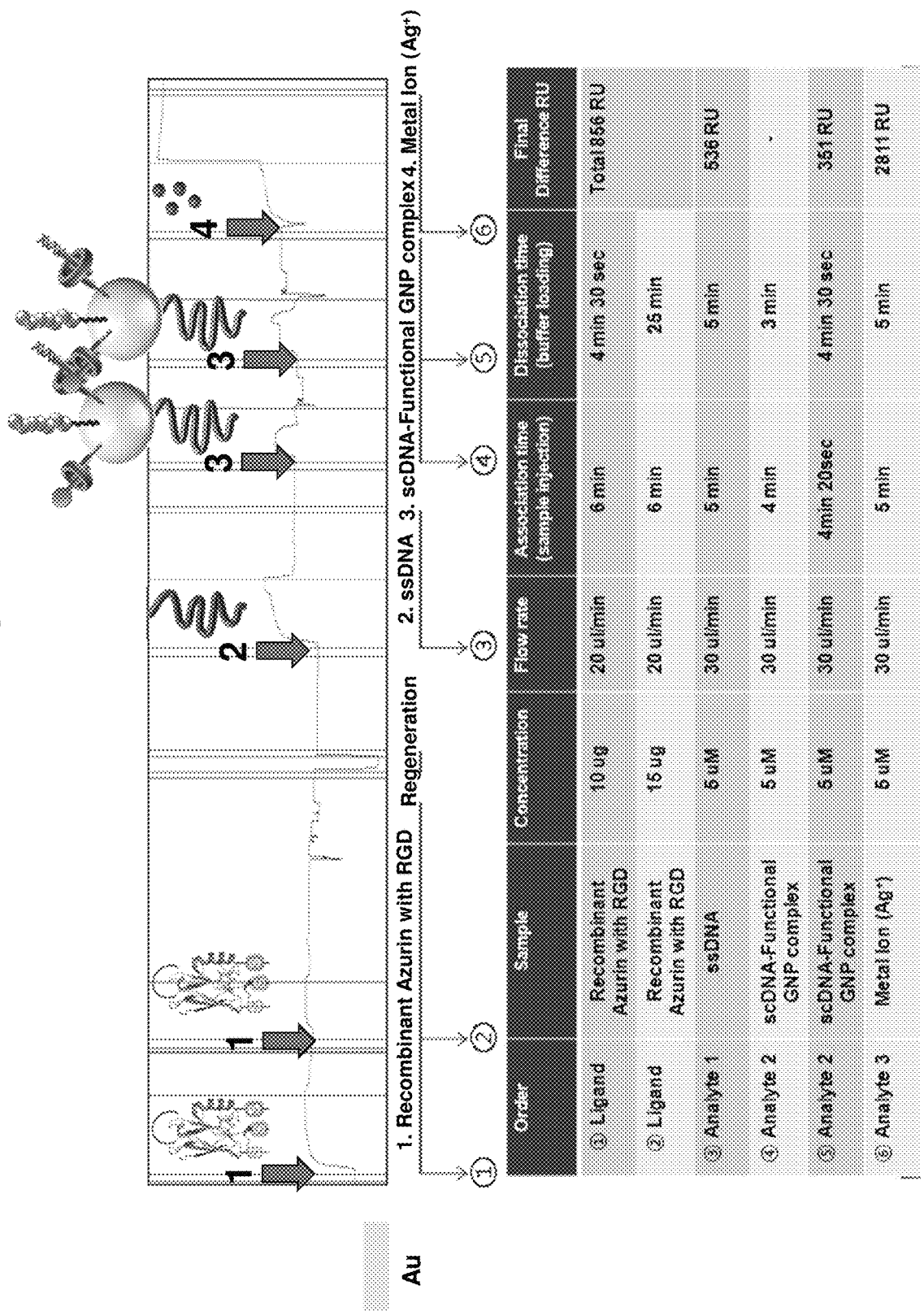
FIG. 9 shows a surface of a biomoletron using flow surface plasmon resonance (flow SPR).

FIG. 9 shows a table regarding flow surface plasmon resonance data and experimental conditions. It was confirmed from the data that the nano-thin film structure of a biomoletron was favorably. The nano-thin film structure means a multi-layered structure of the biomoletron. 1st layer: gold substrate, 2nd layer: azurin protein, 3rd layer: sulfo-SMCC tagged ssDNA, 4th layer: biomoletron top portion (bio-functional nanoparticle-csDNA conjugate, 5th layer: $AgNO_3$ It is shown that the RU value increases as the number of layers in the nano-thin film structure increases. The results confirmed that the nano-thin film structure of the biomoletron was well formed.

Confirmation of Electric Release System Function of Biomoletron

Figure 10A:
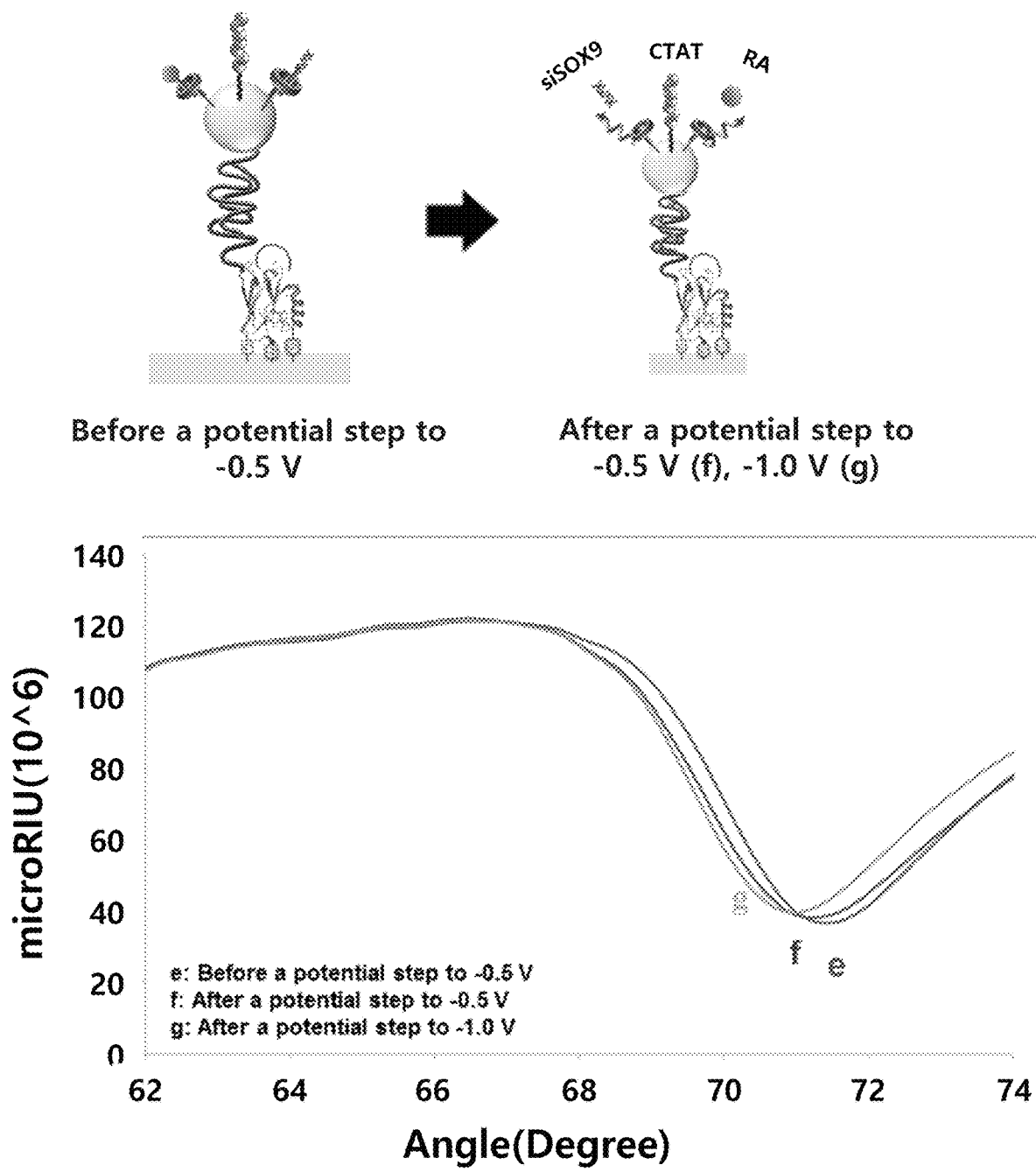
FIG. 10A shows the results of confirming electric release system functions of a biomoletron.
Figure 10B:
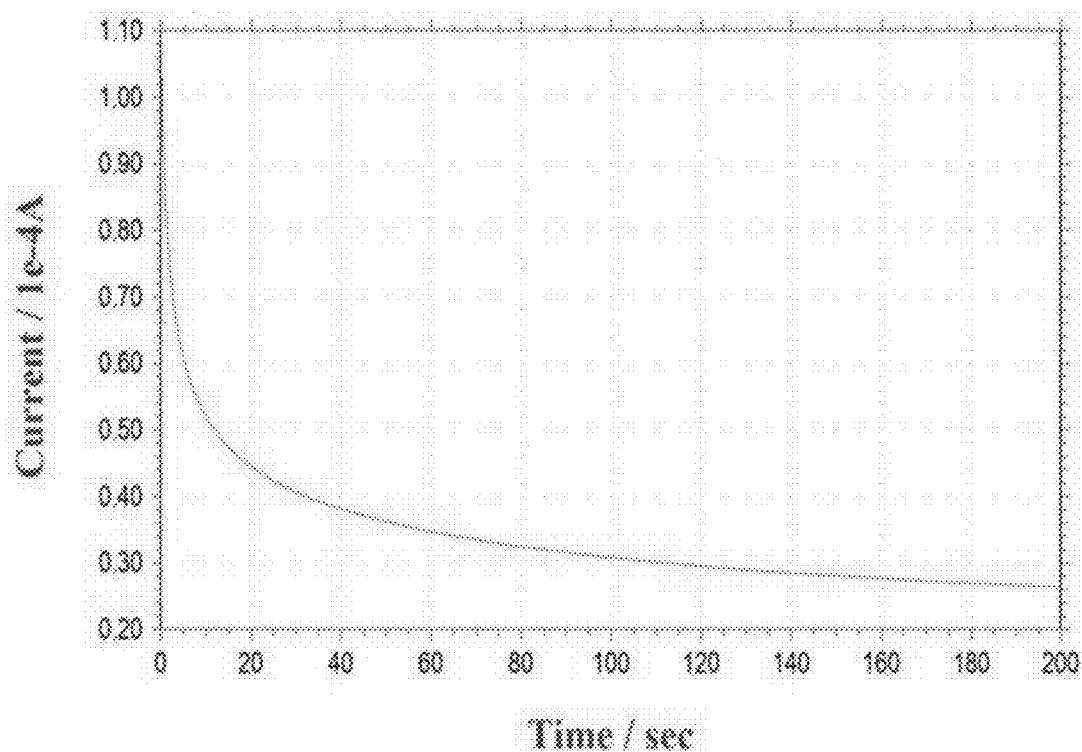
FIG. 10B shows the results of confirming electric release system functions of a biomoletron.
Figure 10C:
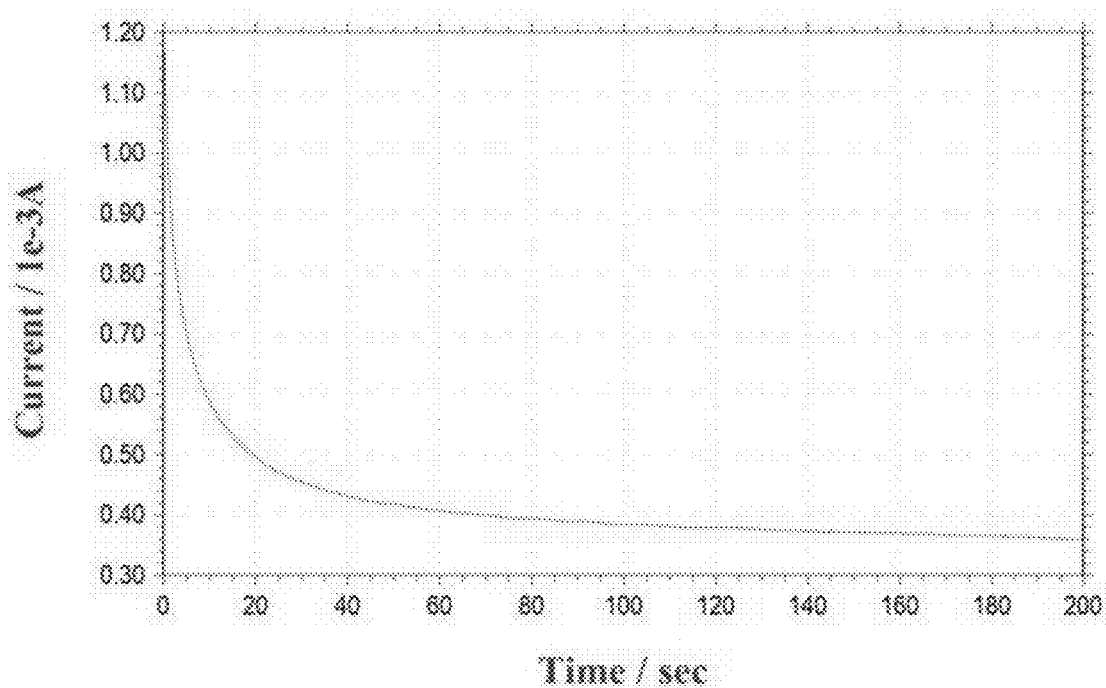
FIG. 10C shows the results of confirming electric release system functions of a biomoletron.
Figure 11A:
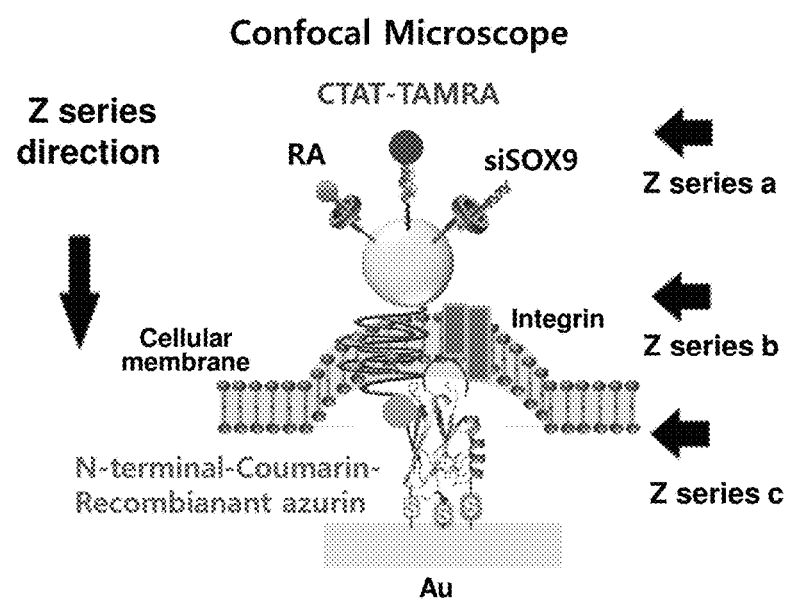
FIG. 11A shows the results of confirming the cell membrane penetration of a biomoletron through three sequential experimental methods.
Figure 11A:
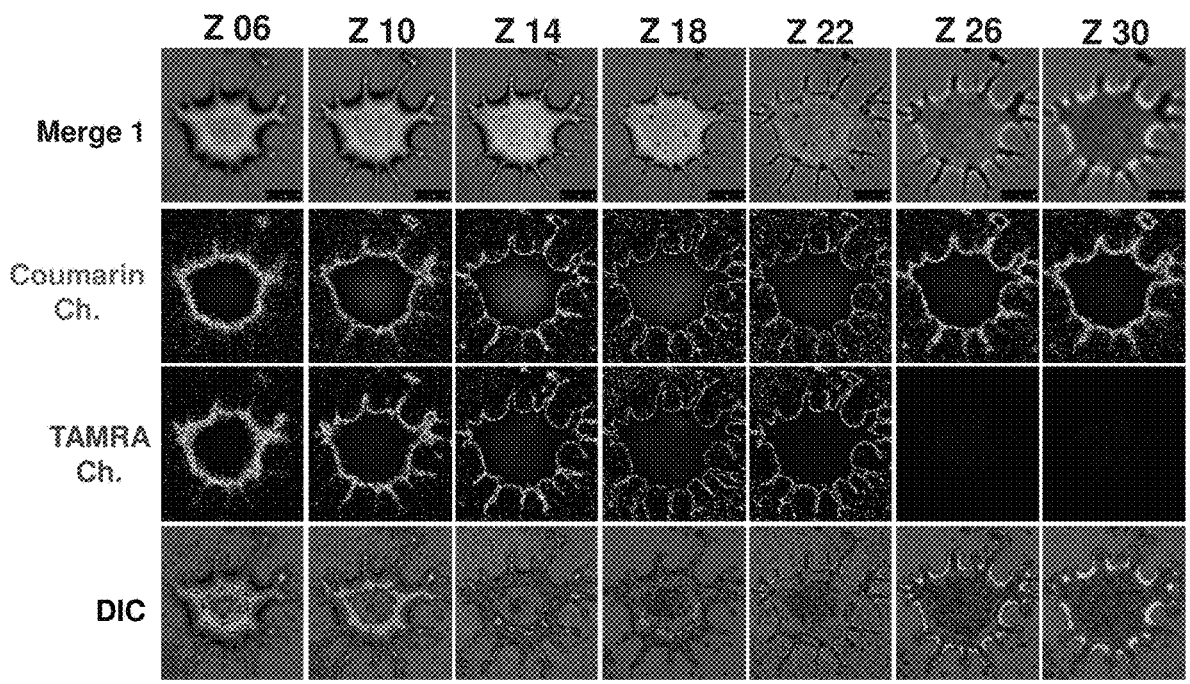
Figure 11B:
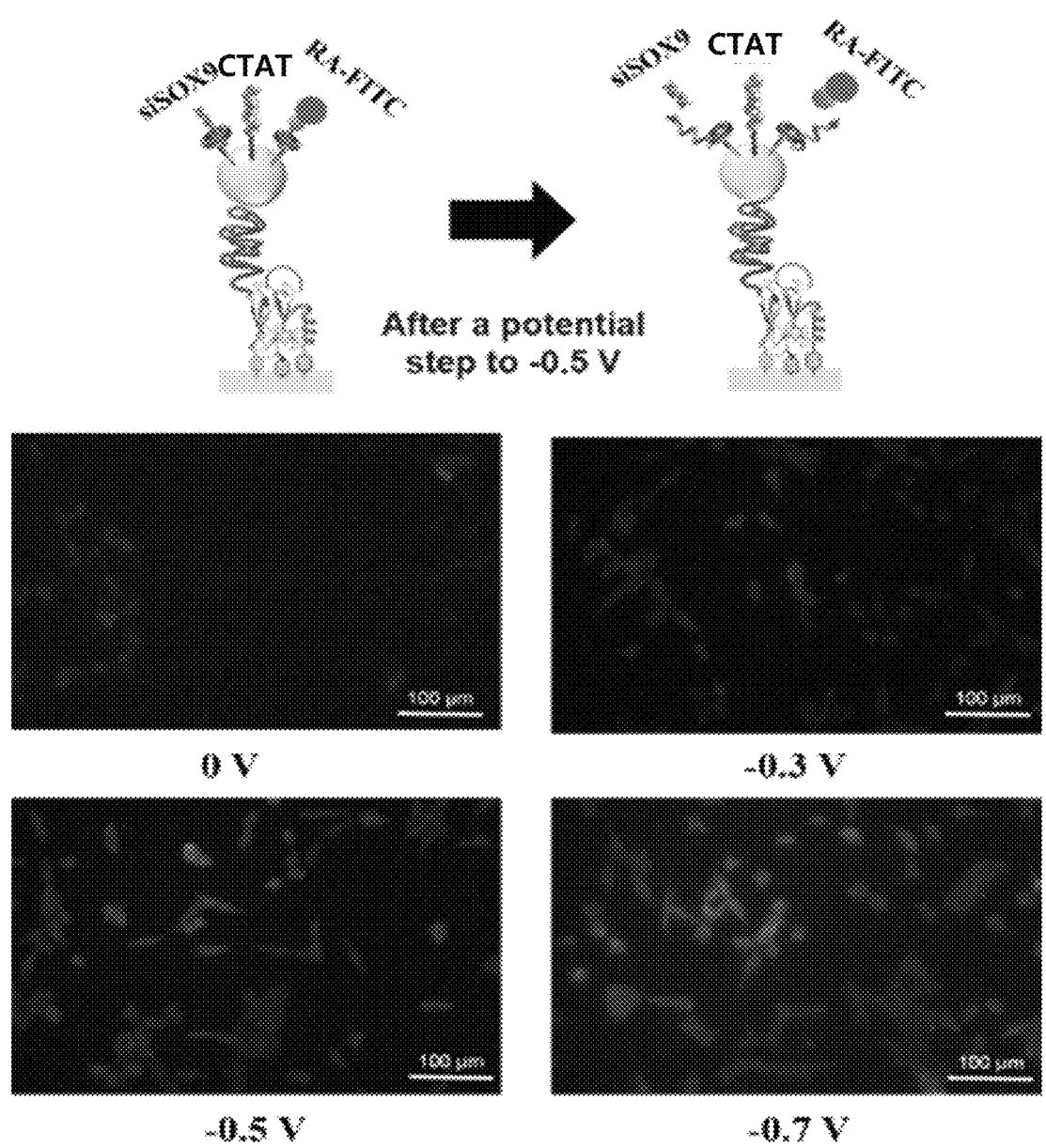
FIG. 11B shows the results of confirming the cell membrane penetration of a biomoletron through three sequential experimental methods.
Figure 11C:
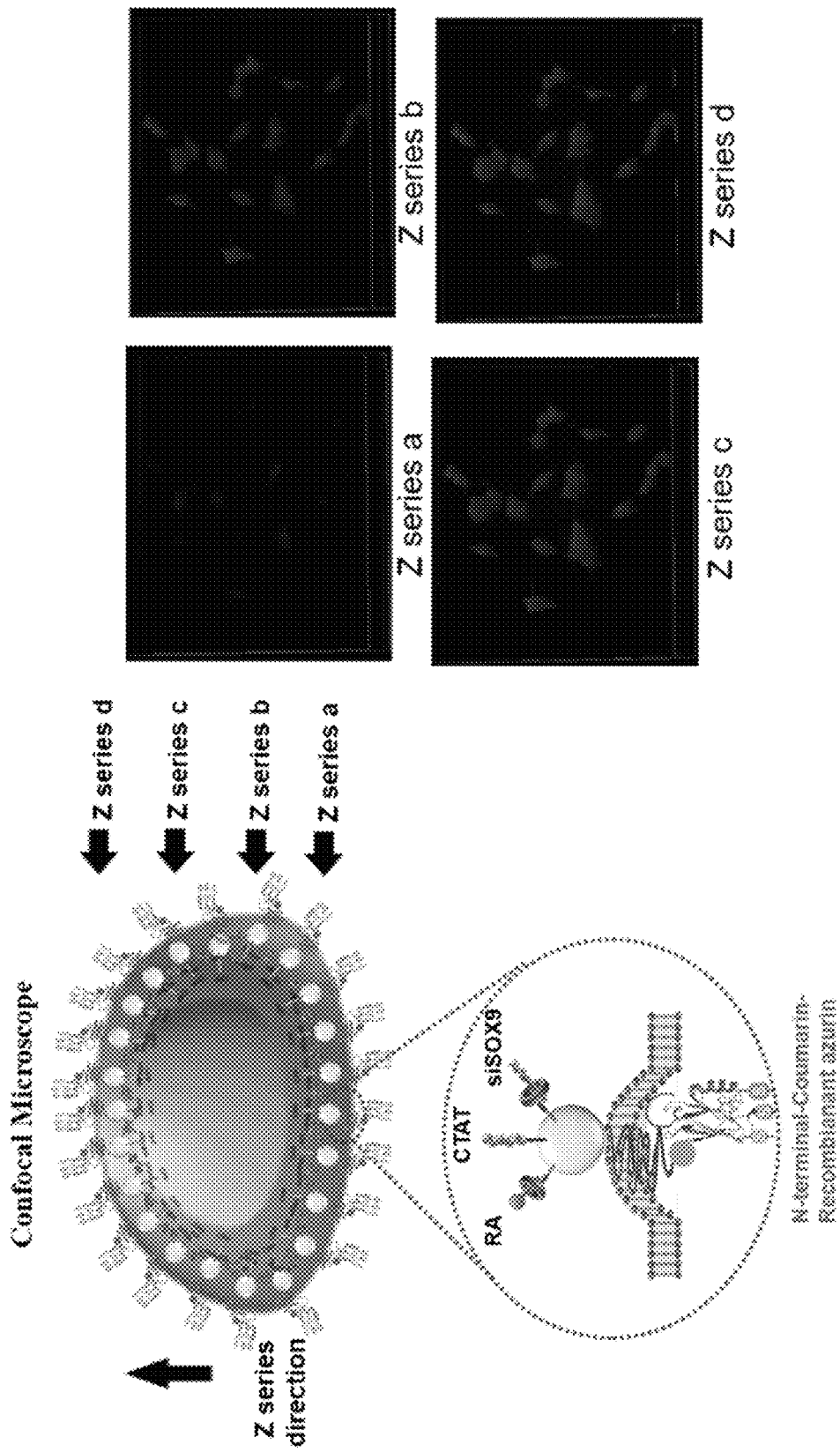
FIG. 11C shows the results of confirming the cell membrane penetration of a biomoletron through three sequential experimental methods.

FIG. 10 shows surface plasmon resonance data for confirming the electric release system function of the biomoletron. In order to investigate the electric release system function of the fabricated three-cysteine and C-terminal RGD peptide-introduced biomoletron nano-thin film structure, amperometric measurement was introduced. The voltage was applied to the biomoletron nano-thin film structure at −0.5 V and −1 V to investigate the electric release system of the functional complex for cell differentiation using SPR. From the results that the SPR angle was reduced after the application of −0.5 V and −1 V compared with that before the application of the voltages, it was confirmed that the electric release system of the functional complex for cell differentiation of the newly fabricated RGD-introduced biomoletron was favorably operated.

Confirmation of Cell Penetration of Biomoletron

FIG. 11 shows cell penetration of a biomoletron through sequential experimental methods. It can be seen from the confocal microscopic data of FIG. 11a that the biomoletron was fabricated near the cell membrane and that there are three possible cases (no penetrating into cell membrane, whole penetrating into cell membrane, and partial penetrating into cell membrane). The fluorescence microscopic data in FIG. 11b show that the FITC entered the cell, and thus the case of "no penetrating into cell membrane" was excluded. The confocal microscopic data in FIG. 11c show that the protein (RGD azurin), which corresponds to a portion of the biomoletron, attached to only the cell surface (integrin), and thus the case of "whole penetrating into cell membrane" was excluded. It can be seen that only the case of "partial penetrating into cell membrane", which is targeted by the present inventors, was ultimately possible.

Confirmation of Biomoletron-Based Neural Stem Cell Differentiation

Figure 12A:
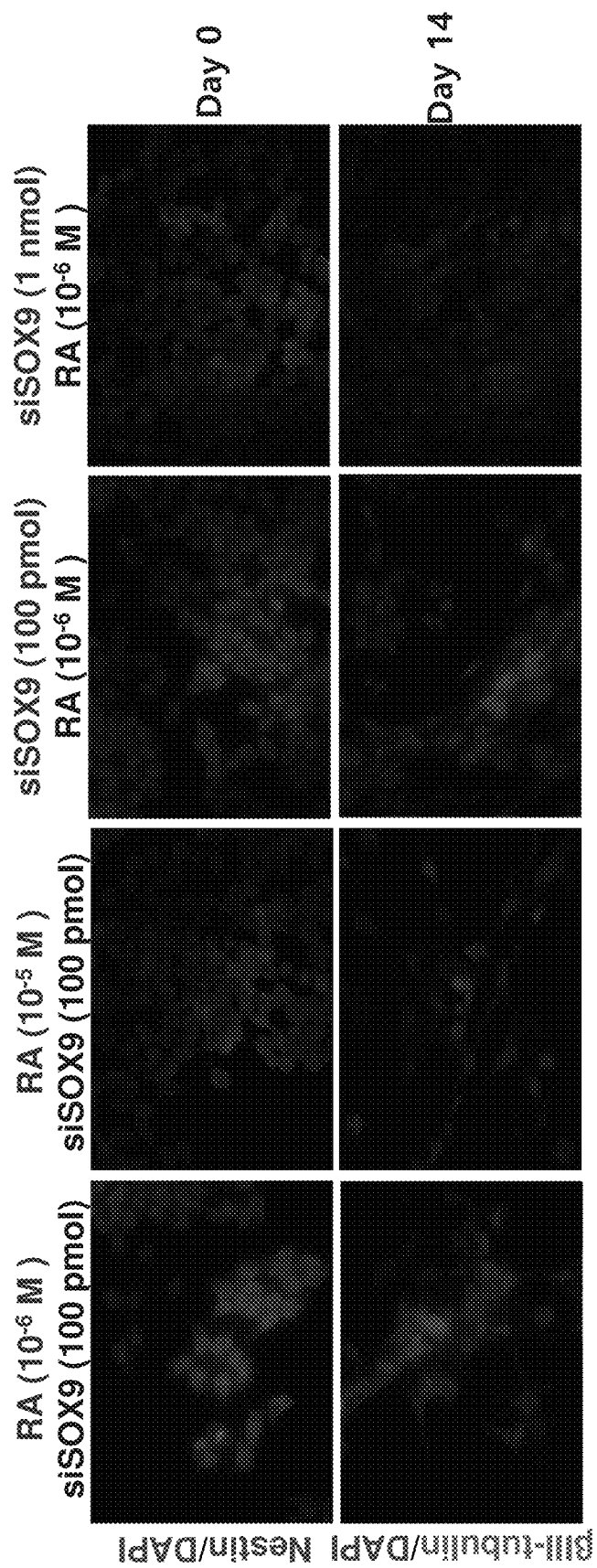
FIG. 12A shows the results of confirming biomoletron-based neural stem cell differentiation.
Figure 12B:
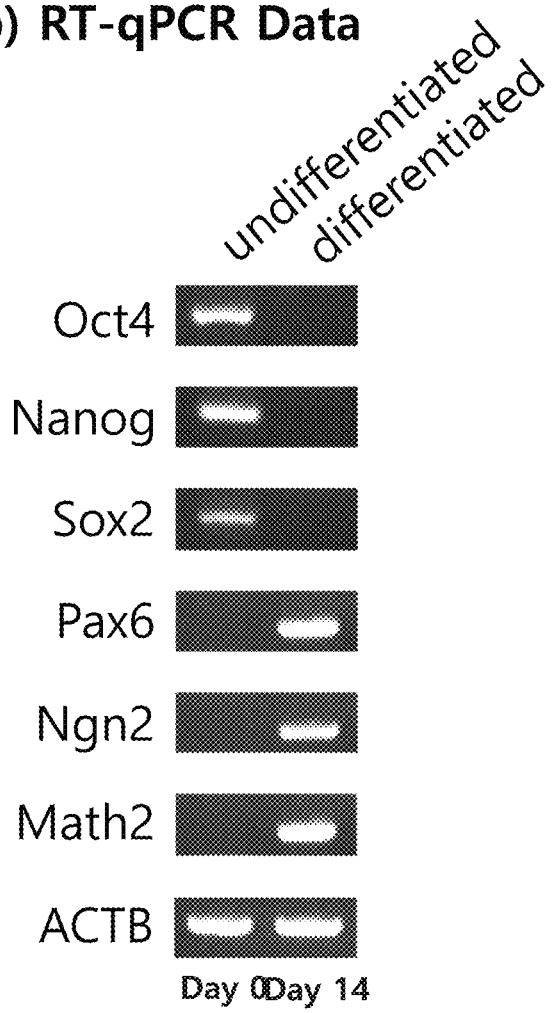
FIG. 12B shows the results of confirming biomoletron-based neural stem cell differentiation.

FIG. 12 shows the results of confirming biomoletron-based neural stem cell differentiation using immunostaining and detection quantitative PCR. FIG. 12a confirmed βIII-tubulin, a stem cell differentiation marker, according to the concentrations of RA and siSOX9 using immunostaining. The biomoletron-based stem cell differentiation was confirmed using detection quantitative PCR (FIG. 12a). It was confirmed that after 14 days of culture, the bands of the stem cell differentiation markers pax6, Ngn2, and Math2 were observed, indicating favorable differentiation.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A bioelectronic device for controlling stem cell differentiation, comprising:
    (a) a protein comprising the amino acid sequence of SEQ ID NO: 2 having a redox potential;
    (b) a first single strand DNA comprising the nucleic acid sequence of SEQ ID NO: 3 binding to the N-terminal of the protein having a redox potential;
    (c) a second single strand DNA comprising the nucleic acid sequence of SEQ ID NO: 4 complimentarily hybridizing with the first single strand DNA to form a double strand DNA;
    (d) a nanoparticle directly conjugated to a terminal of the second single strand DNA; and
    (e) (i) a cell-penetrating peptide and (ii) a differentiation-inducing factor, which are conjugated to the nanoparticle;
    wherein the cell-penetrating peptide is indirectly conjugated through a linker introduced to a surface of the nanoparticle,
    wherein the differentiation-inducing factor is indirectly conjugated through a linker introduced to a surface of the nanoparticle,
    wherein the differentiation-inducing factor is released from the nanoparticle by potential application,
    wherein the double strand DNA further comprises metal ions between mismatch nucleotide pairs, and
    wherein the number of mismatch nucleotide pairs is 1 to 10.

2. The bioelectronic device of claim 1, wherein the protein having a redox potential is directly immobilized to a substrate by having a cysteine residue introduced thereto.

3. The bioelectronic device of claim 1, wherein the protein having a redox potential further comprises, at the C-terminal thereof, a ligand having a binding ability to a cell membrane receptor protein.

4. The bioelectronic device of claim 3, wherein the ligand having a binding ability to a cell membrane receptor protein is at least one ligand selected from the group consisting of RGD(Arg-Gly-Asp) (SEQ ID NO: 8), RGDS(Arg-Gly-Asp-Ser) (SEQ ID NO: 9), RGDC(Arg-Gly-Asp-Cys) (SEQ ID NO: 10), RGDV(Arg-Gly-Asp-Val) (SEQ ID NO: 11), RGES(Arg-Gly-Glu-Ser) (SEQ ID NO: 12), RGDSPASSKP (Arg-Gly-Asp-Ser-Pro-Ala-Ser-Ser-Lys-Pro) (SEQ ID NO: 13), GRGDS(Gly-Arg-Gly-Asp-Ser) (SEQ ID NO: 14), GRADSP(Gly-Arg-Ala-Asp-Ser-Pro) (SEQ ID NO: 15), KGDS(Lys-Gly-Asp-Ser) (SEQ ID NO: 16), GRGDSP(Gly-Arg-Gly-Asp-Ser-Pro) (SEQ ID NO: 17), GRGDTP(Gly-Arg-Gly-Asp-Thr-Pro) (SEQ ID NO: 18), GRGES(Gly-Arg-Gly-Glu-Ser) (SEQ ID NO: 19), GRGDSPC(Gly-Arg-Gly-Asp-Ser-Pro-Cys) (SEQ ID NO: 20), GRGESP(Gly-Arg-Gly-Glu-Ser-Pro) (SEQ ID NO: 21), SDGR(Ser-Asp-Gly-Arg) (SEQ ID NO: 22), YRGDS(Tyr-Arg-Gly-Asp-Ser) (SEQ ID NO: 23), GQQHHLGGAKQAGDV (Gly-Gln-Gln-His-His-Leu-Gly-Gly-Ala-Lys-Gln-Ala-Gly-Asp-Val) (SEQ ID NO: 24), GPR(Gly-Pro-Arg) (SEQ ID NO: 25), GHK(Gly-His-Lys) (SEQ ID NO: 26), YIGSR(Tyr-Ile-Gly-Ser-Arg) (SEQ ID NO: 27), PDSGR(Pro-Asp-Ser-Gly-Arg) (SEQ ID NO: 28), CDPGYIGSR(Cys-Asp-Pro-Gly-Tyr-Ile-Gly-Ser-Arg) (SEQ ID NO: 29), LCFR(Leu-Cys-Phe-Arg) (SEQ ID NO: 30), EIL(Glu-Ile-Leu) (SEQ ID NO: 31), EILDV(Gludle-Leu-Asp-Val) (SEQ ID NO: 32), EILDVPST(Gludle-Leu-Asp-Val-Pro-Ser-Thr) (SEQ ID NO: 33), EILEVPST(Glu-Ile-Leu-Glu-Val-Pro-Ser-Thr) (SEQ ID NO: 34), LDV(Leu-Asp-Val) (SEQ ID NO: 35), and LDVPS(Leu-Asp-Val-Pro-Ser) (SEQ ID NO: 36).

5. The bioelectronic device of claim 1, wherein the protein having a redox potential has a free radical scavenging potential.

6. The bioelectronic device of claim 1, wherein the first single strand DNA indirectly binds to the N-terminal of the protein having a redox potential through a linker.

7. The bioelectronic device of claim 1, wherein the second single strand DNA is directly conjugated to the nanoparticle through a thiol group introduced to a terminal thereof.

8. The bioelectronic device of claim 1, wherein the differentiation-inducing factor is at least one factor selected from the group consisting of siRNA, shRNA, miRNA, ribozyme, DNAzyme, peptide nucleic acid (PNA), antisense oligonucleotide, peptide, antibody, and aptamer.

9. The bioelectronic device of claim 1, wherein the bioelectronic device is integrated into a cell membrane by a ligand having a binding ability to a cell membrane receptor protein, the ligand being introduced to the C-terminal of the protein having a redox potential.

10. A method for controlling stem cell differentiation, the method comprising a step for contacting the bioelectronic device of claim 1 with a stem cell in a stem cell culture medium.

11. A method for fabricating a bioelectronic device for controlling stem cell differentiation, the method comprising:
    (a) providing a self-assembling protein comprising the amino acid sequence of SEQ ID NO: 2 having a redox potential on a substrate;
    (b) binding a first single strand DNA comprising the nucleic acid sequence of SEQ ID NO: 3 to the N-terminal of the protein having a redox potential;
    (c) hybridizing a second single strand DNA comprising the nucleic acid sequence of SEQ ID NO: 4 with the first single strand DNA to form a double strand DNA;
    (d) conjugating a nanoparticle to a terminal of the second single strand DNA; and
    (e) conjugating (i) a cell-penetrating peptide and (ii) a differentiation-inducing factor to a surface of the nanoparticle;
    wherein the cell-penetrating peptide is indirectly conjugated through a linker introduced to a surface of the nanoparticle,
    wherein the differentiation-inducing factor is indirectly conjugated through a linker introduced to a surface of the nanoparticle,
    wherein the differentiation-inducing factor is released from the nanoparticle by potential application,
    wherein the double strand DNA further comprises metal ions between mismatch nucleotide pairs, and
    wherein the number of mismatch nucleotide pairs is 1 to 10.

* * * * *